(12) United States Patent
Dilmanian et al.

(10) Patent No.: US 7,194,063 B2
(45) Date of Patent: Mar. 20, 2007

(54) METHODS FOR IMPLEMENTING MICROBEAM RADIATION THERAPY

(75) Inventors: F. Avraham Dilmanian, Yaphank, NY (US); Gerard M. Morris, Oxford (GB); James F. Hainfeld, Shoreham, NY (US)

(73) Assignee: Brookhaven Science Associates, LLC, Upton, NY (US)

( * ) Notice: Subject to any disclaimer, the term of this patent is extended or adjusted under 35 U.S.C. 154(b) by 7 days.

(21) Appl. No.: 11/054,001

(22) Filed: Feb. 10, 2005

(65) Prior Publication Data

US 2006/0176997 A1 Aug. 10, 2006

(51) Int. Cl.
*A61N 5/10* (2006.01)
(52) U.S. Cl. .......................................... 378/65; 378/64
(58) Field of Classification Search .................. 378/65, 378/64
See application file for complete search history.

(56) References Cited

U.S. PATENT DOCUMENTS

| | | | |
|---|---|---|---|
| 5,339,347 A * | 8/1994 | Slatkin et al. ................. | 378/65 |
| 5,663,999 A | 9/1997 | Siochi | |
| 5,771,270 A | 6/1998 | Archer | |
| 6,366,801 B1 | 4/2002 | Cash, Jr. et al. | |
| 6,442,238 B2 | 8/2002 | Meulenbrugge | |
| 6,512,813 B1 | 1/2003 | Krispel et al. | |
| 6,562,318 B1 | 5/2003 | Filler | |
| 6,620,415 B2 | 9/2003 | Donovan | |
| 6,645,464 B1 * | 11/2003 | Hainfeld ..................... | 424/1.29 |
| 2002/0044959 A1 | 4/2002 | Goetz et al. | |
| 2002/0164288 A1 | 11/2002 | Wilson et al. | |
| 2003/0076927 A1 | 4/2003 | Nakashima et al. | |
| 2004/0005027 A1* | 1/2004 | Nafstadius .................. | 378/65 |
| 2004/0013236 A1 | 1/2004 | Papaioannou | |

FOREIGN PATENT DOCUMENTS

| | | |
|---|---|---|
| WO | WO 96/03155 | 2/1996 |
| WO | WO 97/05904 | 2/1997 |

OTHER PUBLICATIONS

Biston et al., Cure of Fisher Rats Bearing Radioresistant F98 Glioma Treated with cis-Platinum and Irradiated with Monochromatic Synchrotron X-rays, Apr. 1, 2004, Cancer Research, 64, p. 2317-2323.*

(Continued)

*Primary Examiner*—Edward J. Glick
*Assistant Examiner*—John M. Corbett
(74) *Attorney, Agent, or Firm*—Lori-Anne Neiger

(57) ABSTRACT

A method of performing radiation therapy includes delivering a therapeutic dose such as X-ray only to a target (e.g., tumor) with continuous broad beam (or in-effect continuous) using arrays of parallel planes of radiation (microbeams/microplanar beams). Microbeams spare normal tissues, and when interlaced at a tumor, form a broad-beam for tumor ablation. Bidirectional interlaced microbeam radiation therapy (BIMRT) uses two orthogonal arrays with inter-beam spacing equal to beam thickness. Multidirectional interlaced MRT (MIMRT) includes irradiations of arrays from several angles, which interleave at the target. Contrast agents, such as tungsten and gold, are administered to preferentially increase the target dose relative to the dose in normal tissue. Lighter elements, such as iodine and gadolinium, are used as scattering agents in conjunction with non-interleaving geometries of array(s) (e.g., unidirectional or cross-fired (intersecting) to generate a broad beam effect only within the target by preferentially increasing the valley dose within the tumor.

21 Claims, 9 Drawing Sheets

OTHER PUBLICATIONS

Robar et al., Tumour dose enhancement using modified megavoltage photon beams and a contrast media, Jul. 4, 2002, Phys. Med. Biol., 47, p. 2433-2449.*

Schweizer et al., Tissue lesions caused by microplanar beams of synchrotron-generated x-rays in *Drosphila melanogaster*, 2000, vol. 76, No. 4, p. 567-574.*

Brauer-Krisch et al., New irradiation geometry for microbeam radiation therapy, Jul. 22, 2005, Phys. Med. Biol., 50, p. 3103-3111.*

Brauer-Krisch et al., "Exploiting Geometrical Irradiation Possibilities in MRT Application", Apr. 8, 2005, Nuclear Instruments and Methods in Physics Research A, vol. 548, Issue 1-2, pp. 69-71.*

Brauer-Krisch et al., "New Irradiation Geometry for Microbeam Radiation Therapy", Jun. 22, 2005, Phys. Med. Biol., 50, pp. 3103-3111.*

Slatkin D. N., "Uniaxial and biaxial trradiation protocols for microbeam radiation therapy", Jun. 11, 2004, Phys. Med. Biol., 49, Notes N203-N204.*

Hainfeld, et al. "The Use of Gold Nanoparticles to Enhance Radiotherapy in Mice," *Phys. Med. Biol.* 49(18):N309-N315 (2004).

Laissue, et al., "Microbeam Radiation Therapy (MRT)," Institute of Pathology.

Slatkin, et al., "Microbeam Radiation Therapy," 1992 Am. Assoc. Phys. Med., Med. Phys. 19 (6), pp. 1395-1400 (Nov./Dec. 1992).

Slatkin, et al., "Microplanar Beam Radiotherapy (MRT) of Malignant Brain Tumors In Rats," Brookhaven National Laboratory, National Synchrotron Light Source Annual Activity Report, p. B-132 (Apr. 1994).

Slatkin, et al., "Design of a Multislit, Variable Width Collimator for Microplanar Beam Radiotherapy," 1995 American Institute of Physics, Rev. Sci. Instrum. 66(2), pp. 1459-1460 (Feb. 1995).

Slatkin, et al., "Subacute Neuropathological Effects of Microplanar Beams of X-rays from a Synchrotron Wiggler," Proc. Natl. Acad. Sci. USA, vol. 92, pp. 8783-8787 (Sep. 1995).

Dilmanian, et al., "Microbeam Irradiation of Duck Embryo Brains: Relevance to Microbeam Radiation Therapy (MRT) of Brian Tumors In Infants," Brookhaven National Laboratory, National Synchrotron Light Source Annual Activity Report, p. B-140 (May 1997).

Laissue, et al., "Neuropathology of Ablation of Rat Gliosarcomas And Contiguous Brain Tissues Using A Microplanar Beam of Synchrotron-Wiggler-Generated X Rays," Int. J. Cancer: 78, 654-660 (1998).

Laissue, et al., "Microbeam Radiation Therapy," SPIE—The International Society for Optical Engineering, Medical Applications of Penetrating Radiation, vol. 3770, pp. 38-45 (Jul. 22-23, 1999).

Schweizer, et al., "Tissue Lesions Caused by Microplanar Beams of Synchrotron-Generated X-rays in *Drosophila melanogaster*," Int. J. Radiat. Biol. 2000, vol. 76, No. 4, pp. 567-574 (1999).

Dilmanian, et al., "Response of Avian Embryonic Brain To Spatially Segmented X-Ray Microbeams," Cellular and Molecular Biology™, vol. 47, No. 3, pp. 485-493 (2000).

Solberg, et al., "Monoenergetic X-rays Improve the Therapeutic Ratio in X-Ray Phototherapy of Brain Tumors," Departments of Radiation Oncology and Radiological Sciences, UCLA School of Medicine, Los Angeles, USA, Medical Applications of Synchrotron Radiation (Mar. 1-3, 2001).

Balosso, et al., "Medical Applications of Synchrotron Radiation: Anti-Cancer Radiotherapy," Workshop on Medical Applications of Synchrotron Radiation, ESRF—Mar. 1-3, 2001, Grenoble, France, pp. 14-15 (2001).

Blattmann, et al., "Microbeam Radiation Therapy, Present Status," Workshop on Medical Applications of Synchrotron Radiation, ESRF—Mar. 1-3, 2001, Grenoble, France, pp. 14-15 (2001).

Le Bas, et al., "Center Hospitalier Univeeersitaire (CHU) and Université Joseph Fourier Overview," Workshop on Medical Applications of Synchrotron Radiation, ESRF—Mar. 1-3, 2001, Grenoble, France, pp. 14-15 (2001).

Laissue, et al., "The Weanling Piglet Cerebellus: A Surrogate for Tolerance to MRT (Microbeam Radiation Therapy) in Pediatric Neuro-Oncology," SPIE—The International Society for Optical Engineering, Penetrating Radiation Systems and Applications III, vol. 4508, pp. 65-73 (Aug. 1-2, 2001).

Dilmanian, et al., "Response of Rat Intracranial 9L Gliosarcoma to Microbeam Radiation Thearapy," Neuro-Oncology, pp. 26-38 (Jan. 2002).

Dilmanian, et al., "Murine EMT-6 Carcinoma: High Therapeutic Efficacy of Microbeam Radiation Therapy," Radiation Research, pp. 1-30 (Aug. 6, 2002).

Zhong, et al., "Correlation between the Microscopic and Macroscopic Effects of Microbeam Radiation Therapy (MRT) on the Rat Skin," National Synchrotron Light Source Annual Activity Report, Abstract No. zhon 173 (2001).

Zhong, et al., "Evaluation of the Radiation Enhancer, Motexafin Gadolinium (MGd), for Microbeam Radiation Therapy of Subcutaneous Mouse EMT-6," National Synchrotron Light Source Annual Activity Report, Abstract No. zhon 193 (2001).

Zhong, et al., "LEL/BrdU Double Staining: A Quantitative Study of Endothelial Cell Proliferation in the Rat Cerebellum Irradiated with X-ray Microbeams," National Synchrotron Light Source Annual Activity Report, Abstract No. zhon 194 (2001).

Dilmanian, et al., "Design of a Dedicated Medical Synchrotron X-ray Facility Primarily for Microbeam Radiation Therapy (MRT)" National Synchrotron Light Source Annual Activity Report, Abstract No. dilm437 (2001).

Walker, S.J., "Boron neutron capture therapy; principles and prospects", *Radiography*, 4:211-219 (1998).

Friedman, et al., "Stereotactical Radiosurgical Pallidotomy and Thalamotomy with the Gamma Knife: MR Imaging Findings with Clinical Correlation—Preliminary Experience", *Radiology*, 212:143-150 (1999).

Renier, et al., "A white-beam fast-shutter for microbeam radiation therapy at the ESRF", *Nuclear Instruments and Methods in Physics Research A*, 479:656-660 (2002).

Chu, et al., "Human neural stem cell transplantation reduces spontaneous recurrent seizures following pilocarpine-induced status epilepticus in adult rats", *Brain Research*, 1023:213-221 (2004).

Cao, et al., "Use of Magnetic Resonance Imaging to Assess Blod-Brain/Blood-Glioma Barrier Opening During Conformal Radiotherapy", *Journal of Clinical Oncology*, vol. 23, No. 18 (2005).

* cited by examiner

METHODS FOR IMPLEMENTING MICROBEAM RADIATION THERAPY

This invention was made with Government support under contract number DE-AC02-98CH10886, awarded by the U.S. Department of Energy. The Government has certain rights in the invention.

FIELD OF THE INVENTION

The present invention relates generally to methods for performing microbeam radiation therapy, primarily for tumor treatment, and more particularly to methods of using microbeam arrays to produce a broad beam effect only within the tumor thus increasing the therapeutic effect of microbeam radiation therapy.

BACKGROUND OF THE INVENTION

Cancer continues to be one of the foremost health problems. Conventional treatments such as surgery, chemotherapy and radiation therapy have exhibited favorable results in many cases, while failing to be completely satisfactory and effective in all instances. For example, the effectiveness of orthodox radiation therapy on deep pulmonary, bronchial, and esophageal tumors is limited by the risk of radiation pneumonitis.

The goal of radiation therapy is generally to maximize the therapeutic index, which is defined as the ratio of the maximum tolerable dose beyond which unacceptable levels of normal tissue toxicity would occur, to the minimal dose required for effective tumor control. This goal is particularly difficult to achieve in treating central nervous system (CNS) tumors. Malignant gliomas which include astrocytomas, oligodendrogliomas and glioblastoma represent about 60% of all primary brain tumors, with an incidence of over 8,000 cases per year. The survival statistics of patients with high grade gliomas in the brain, or lower grade gliomas and metastatic tumors in the spinal cord have not improved appreciably in recent years using conventional surgical techniques and conventional radiotherapy. The doses that can be delivered to malignant CNS tumors are limited by the tolerance of normal brain and spinal cord to radiation. For higher grade CNS tumors, radiation is generally offered only as a palliative rather than curative therapy. For lower grade CNS tumors, the ratio of radiotherapy doses that produce normal CNS toxicity and those that control the tumor is so close that it often renders radiotherapy ineffective, or results in neurological complications from radiotoxicity to the normal CNS surrounding the tumor. In addition, tolerance of the normal CNS to re-treatment, if necessary, will be lower.

It is well known to those skilled in the art that the threshold dose, or maximum tolerable dose before neurological and other complications of radiotherapy arise, increases as irradiated volumes of tissue are made smaller. Such observations eventually led to the development of grid radiotherapy using grids or sieves for spatial fractionation of X-rays. Recently, a much less familiar alternative form of radiation therapy, known as microbeam radiation therapy (MRT), has been investigated to treat tumors such as these for which the conventional methods are ineffective or associated with a high risk factor.

The concept of MRT was introduced in U.S. Pat. No. 5,339,347 to Slatkin et al. MRT differs from conventional radiation therapy by employing arrays of parallel planes of radiation, which are at least one order of magnitude smaller in thickness (or diameter if, in the rare case, parallel cylindrical beams are used rather than planar beams) than the smallest radiation beams in current conventional clinical use. These very thin microbeams, which are also called microplanar beams, can be generated using the high intensity X-ray beams that are currently generated at electron synchrotron storage rings.

The optimum thickness of the individual microbeams used in the array is dependent upon the capacity of tissue surrounding a beam path to support the recovery of the tissue injured by the beam. It has been postulated that segments of the capillary blood vessels destroyed in the direct paths of the individual microbeams are replaced by the microvasculature regeneration effected by the capillary segments surviving between individual microbeams.

For example, normal rat-brain tissues have been shown to display an unusually high resistance to damage when irradiated with such beams, if the individual microbeams of tens of micrometers in thickness are delivered at skin-entrance absorbed doses of up to about 5000 Gy. Also, arrays of microbeams with 20–90 micrometers (μm) of beam width and about 100–300 μm of center-to-center spacing of adjacent beams are tolerated up to 625 Gy of in-beam incident doses. This sparing effect has been attributed to rapid repair of microscopic lesions by unirradiated adjacent cells in the capillary blood system and the glial system. Because of this high resistance of normal brain tissues to very high radiation doses, multiple parallel microplanar beams of uniform microscopic thickness (in the range of tens of micrometers) and macroscopic breadth or width (in the centimeter range) have been proposed for treating brain tumors in human infants, for example, in Slatkin et al., "Subacute Neuropathological Effects of Microplanar Beams of X-rays from a Synchrotron Wiggler," Proc. Natl. Acad. Sci. USA, Vol. 92, pp. 8783–8787 (1995b), which is incorporated herein by reference.

The Slatkin et al. patent discloses the segmentation of a broad beam of high energy X-ray into microbeams (beams of thickness less than about 1 millimeter (mm)), and a method of using the microbeams to perform radiation therapy. The target tissue, e.g., a tumor, receives a summed absorbed dose of radiation exceeding a maximum absorbed dose tolerable by the target tissue by crossing or intersecting microbeams at the target tissue. The irradiated in-path non-target tissue is exposed only to non-crossing beams. Non-target tissue between the microbeams receives a summed absorbed dose of radiation less than the maximum tolerable dose, i.e., a non-lethal dose to non-target tissue. In this way, the irradiated non-target tissue in the path of the microbeam is allowed to recover from any radiation injury by regeneration from the supportive cells surviving between microbeams. The probability of radiation-induced coagulative necrosis in the irradiated normal, non-targeted tissue is also lowered due to the non-crossing beam geometry in the non-target tissue, allowing for lower levels of radiation to the non-target tissue. Using microbeam radiation therapy in this way helps improve the effectiveness of clinical radiation therapy, especially for deep-seated tumors.

The microbeams geometries disclosed in the Slatkin et al. patent are of two basic types. Exposure of the target may be accomplished by a unidirectional array of microbeams which may be parallel or may converge at the target. Alternatively, two arrays of microbeams originating from different directions may be "cross-fired," and intersect at an isocenter in the target tissue. The microbeams within each array may be substantially parallel to each other or may converge at an isocenter within the target.

Radiation-enhancing agents have been used experimentally in radiation therapy. For example, radiation sensitizers which use pharmaceutical compounds with gadolinium in them, such as motexafin gadolinium (MGd), have been used to enhance the radiation damage to the target tissue by increasing the amount of free radicals produced by the radiation. These sensitizers, however, are commonly highly toxic, and care must be taken not to administer too large of a quantity of these compounds to a subject. Even with careful administration, an unwanted risk to the subject is imposed by this method, because of variations in tolerance levels among subjects.

In a similar way, contrast agents have been used in experimental conventional radiation therapy in a type of phototherapy commonly called photon activation therapy. Photon activation therapy typically includes two steps: accumulation of a substance of high atomic number within the target tissue and localized activation of the substance with an appropriately tuned monochromatic photon source. In the absence of activation, the substance, referred to herein as an activating substance or an activating radiation enhancer, is preferably non-toxic. In addition, the required irradiation dose to activate the substance should be below the minimum absorbed dose which would be lethal to non-target tissue minimally containing the activating substance. Only the combination of both the accumulation of the substance in the target tissue and direct irradiation of the target tissue with the monochromatic source, therefore, leads to the desired synergistic effect of ablating the targeted tumor.

Typically, a monochromatic X-ray beam is tuned to just above (or slightly more above) the so-called K-edge energy of the substance, for high absorption of tissue containing the activating radiation enhancer. The substances conventionally used are imaging contrast agents known to be highly absorbing of the incident monochromatic beam. In one example, iodine is a known activating substance which can be injected intravenously into a subject and used in photon activation therapy to treat a brain tumor. Due to blood brain barrier breakdown, the iodine preferentially accumulates in the tumor. The monochromatic X-ray beam is tuned to be above the K-edge of iodine (just above or shortly above it), which is about 33.2 keV, and directed at the site of the tumor, in a dose not exceeding normal tissue tolerance (in the absence of activation).

The dose and the concentration of iodine in the tumor is typically adjusted such that minimal damage is sustained by normal tissue in the path of a conventional X-ray broad beam, while an enhanced therapeutic dose is delivered at the site of the tumor because of the highly absorbing effect of the contrast agent. In practice, however, there is still the risk of radiation-induced tissue necrosis by the broad X-ray beam.

Experiments have been performed to combine use of the radiation enhancer motexafin gadolinium (MGd) for photon activation therapy with cross-planar microbeam radiation therapy to provide crossing beams and thus to further enhance the X-ray dose only at the site of the target tumor, as described in Zhong, et al., "Evaluation of the Radiation Enhancer, Motexafin Gadolinium (MGd), for Microbeam Radiation Therapy of Subcutaneous Mouse EMT-6," National Synchrotron Light Source Activity Report (2001) Abstract No. zhon193. The MGd compound was used in these experiments for its chemical properties as an enhancer of free radicals in tissue. It is extremely toxic, however, and has a very small amount of gadolinium in it. Therefore, only a small amount can be administered to the subject.

There is a need in the prior art, therefore, for more efficient methods of radiation therapy which greatly enhance the therapeutic dose at the tumor, while simultaneously maintaining a safe dose to normal tissue.

SUMMARY OF THE INVENTION

The present invention, which addresses the needs of the prior art, relates to more efficient methods of radiation therapy which greatly enhance the therapeutic dose and damage to target tissue, such as a tumor, while simultaneously reducing damage to normal tissue in the path of the irradiating beam. This result is achieved by providing a different type of radiation, i.e., a broad beam effect, to the tumor than to the normal tissue in the beam path.

A method of the present invention of performing radiation therapy on a subject includes delivering a therapeutic dose of high energy electromagnetic radiation substantially only to a target tissue by generating a broad beam radiation effect substantially only within the target tissue. The dose is delivered by irradiating the target tissue with at least one array of microbeams. The broad beam radiation effect is not generated in non-target normal tissue. The at least one array includes at least two spatially distinct parallel microbeams.

The high energy electromagnetic radiation may include X-ray radiation. The X-ray radiation may be produced either by a synchrotron electron storage ring or by a bremsstrahlung source. Preferably, the X-ray radiation includes bremsstrahlung radiation.

The target tissue may include one of an ocular tumor and a brain tumor.

The broad beam effect is generated within the target tissue or tumor using one of two techniques: the first uses interleaved microbeams at the target tissue to form a substantially continuous broad beam of radiation substantially within the tumor; and the second preferably uses non-interleaved microbeam array(s) in combination with a radiation scattering agent administered to the target tissue, to preferentially raise the valley dose within the target tissue, e.g., the tumor. Here, the radiation scattering agent produces an in-effect broad beam in the tumor by raising the valley dose of the microbeam array to the level that it approaches the broad-beam irradiation dose that is necessary to ablate tumor; the distinct direct microbeam peaks present in the array do not interfere with the in-effect broad beam radiation produced.

In the first technique, the therapeutic dose is delivered by irradiating the target tissue with at least two non-intersecting arrays of microbeams and interleaving these arrays only within the target tissue to form a substantially continuous broad beam only within the target tissue.

Each of the at least two parallel, spatially distinct microbeams preferably includes a beam thickness, a beam width and a beam plane. The beam planes of the at least two non-intersecting arrays are preferably parallel to each other. Each array further includes an inter-beam spacing between adjacent microbeams. The inter-beam spacing between adjacent microbeams in each of the arrays is substantially equal to or greater than the beam thickness. The interleaving of the arrays may be performed by: irradiating the target tissue in a first irradiation direction with a first one of the at least two non-intersecting arrays of microbeams; angularly displacing a second one of the at least two non-intersecting arrays from the first one by rotating one of the subject and a source generating the at least two non-intersecting arrays about an axis positioned through a center of the target tissue, where the axis is perpendicular to the parallel beam planes; translating the second array in a direction perpendicular to the beam planes of the microbeams by a distance substantially equal to or greater than the beam thickness; and irradiating the target tissue in a second irradiation direction with the second one of the at least two non-intersecting arrays.

The inter-beam spacing is preferably substantially equal to the beam thickness, and the translating distance is preferably substantially equal to the beam thickness.

The at least two non-intersecting arrays of microbeams may be angularly displaced by about ninety (90) degrees. This particular configuration, when using two arrays, is referred to as bidirectional interlaced microbeam radiation therapy (BIMRT).

In another interleaved configuration referred to as multi-directional interlaced microbeam radiation therapy (MIMRT), a target tissue is irradiated from multiple directions while forming a substantially continuous beam only within the target tissue using interleaved microbeam arrays. In this method, the steps of angularly displacing, translating, and irradiating are repeated a number of times, so that a total number of n irradiations covers a 360° angular space around the target tissue. In MIMRT, the amount of each angular displacement is preferably equal to 360 degrees divided by n. In addition, the act of translating includes translating by a distance substantially equal to the beam thickness, wherein the inter-beam spacing between microbeams in each array is substantially equal to the product of the beam thickness and (n−1).

Any of the interlaced MRT techniques of the present invention, e.g., BIMRT and MIMRT, may further include providing a concentration of a radiation contrast agent substantially only to the target tissue for preferential X-ray absorption. The concentration enhances an in-beam dose of the high energy electromagnetic radiation in each of the at least two parallel, spatially distinct microbeams of the at least two non-intersecting arrays interleaved substantially only within the target tissue.

The radiation contrast agent for use with interlaced MRT preferably has a K-edge of at least 65 keV.

The radiation contrast agent of the above interlaced methods may include at least one of tungsten and gold.

Preferably, the radiation contrast agent includes metal nanoparticles, which may include at least gold and/or tungsten.

In the second technique of the present invention, a therapeutic dose of high energy electromagnetic radiation is delivered substantially only to a target tissue by generating a broad beam radiation effect only within the target tissue. The act of delivering includes irradiating the target tissue with at least one array of microbeams having at least two parallel, spatially distinct microbeams. The method further includes providing a concentration of a radiation scattering agent substantially only to the target tissue. The radiation scattering agent scatters the high energy electromagnetic radiation substantially sideways to an irradiation direction of the individual microbeams, thus raising a valley dose, i.e., the dose between each of the at least two parallel, spatially distinct microbeams, substantially only within the target tissue. The raising of the valley dose between microbeams in the array relative to the in-beam dose provides the broad beam effect substantially only within the target tissue.

In this technique, the at least one array is preferably either a single microbeam array or at least two cross-fired arrays that intersect substantially only within the target tissue. In addition, the at least two parallel spatially distinct microbeams in the array(s) include a beam thickness and an inter-beam spacing. In this method, the inter-beam spacing is not limited to some proportional number of beam thicknesses, as in the interlaced methods, but should be greater than a spacing that would induce damage to normal tissue irradiated by the microbeam array(s).

The radiation scattering agent may include at least one of gadolinium and iodine.

The act of delivering in any of the methods of the present invention may also include administering the therapeutic dose over more than one session in dose fractionations. A sum of the dose fractionations is substantially equal to the therapeutic dose.

The sessions may be separated over a time interval within a range of about 12 hours to about five days.

The beam thickness of the microbeam array used in any of the methods of the present invention may be substantially in a range greater than or equal to about 20 micrometers and less than or equal to about 1000 micrometers.

The beam thickness may be substantially in a range greater than or equal to about 500 micrometers and less than or equal to about 1000 micrometers.

In one particular embodiment of the present invention, the target tissue includes ocular melanoma and the high energy electromagnetic radiation includes X-ray radiation. For radiation therapy applied to ocular melanomas, each of the at least two parallel, spatially distinct microbeams in each array preferably includes a dose fall off of less than about 30 micrometers.

As a result, the present invention provides more efficient methods of radiation therapy by employing microbeams in particular geometries, including BIMRT and MIMRT, or by using microbeam array(s) in combination with a radiation scattering agent to produce a broad beam effect only within a target tissue. The methods may include the use of contrast agents, which are preferentially up-taken by the tumor tissue, of two different types: (a) those including heavy elements to enhance in-beam absorption of microbeam radiation, preferably used with the interlaced technique of the present invention, e.g., BIMRT and MIMRT; and (b) those including lighter elements to produce scattering of microbeam radiation, preferably used with non-interleaving microbeams to preferentially increase the valley dose within the target tissue. Both types of agents will greatly enhance the therapeutic dose and contribute to a broad beam effect at the site of the tumor. Safe doses are maintained to normal tissue in the path of the irradiating beam by the particular geometries of irradiation provided using microbeams.

BRIEF DESCRIPTION OF THE DRAWINGS

FIG. 2b is a partial side view of a MIMRT array similar to the one used in FIG. 2a.

DETAILED DESCRIPTION OF THE INVENTION

The present invention provides more efficient methods of performing radiation therapy, which employ microbeams in particular geometries and with the aid of various contrast agents to generate a broad beam effect substantially only within a target tissue.

A method of performing radiation therapy on a subject according to the present invention includes delivering a therapeutic dose of high energy electromagnetic radiation, using at least one microbeam array, substantially only to a volume of target tissue by generating a broad beam effect substantially only within the target tissue. Normal tissue in the in-beam part of the non-target tissue, on the other hand, does not encounter this broad beam radiation, and, therefore, does not receive a harmful dose. Accordingly, non-target tissue is spared from the radiation-induced damage which is typical of conventional broad-beam radiation methods.

In particular, the present invention provides a method of safely delivering a therapeutic dose of high energy electromagnetic radiation to a target volume of tissue, by interleaving two or more microbeam arrays only within the target volume, thus creating a substantially continuous broad beam only within the target, e.g., a tumor.

In addition, the present invention provides a method of delivering the therapeutic dose by generating an in-effect broad beam dose preferably using a single unidirectional microbeam array or non-interleaved, cross-fired arrays in combination with a radiation scattering agent administered to the tumor. The scattering agent scatters the incident radiation substantially sideways to the incident beam, creating the broad beam effect only within the tumor by raising the valley dose (dose between microbeams) within the tumor. Here, the radiation scattering agent produces an in-effect broad beam in the tumor by raising the valley dose of the microbeam array to the level that it approaches the broad-beam irradiation dose that is necessary to ablate tumor; the distinct direct microbeam peaks present in the array do not interfere with the in-effect broad beam radiation produced.

The high energy electromagnetic radiation may be of any type effective for tumor control or ablation, for example, X-ray radiation.

Figure 1A:
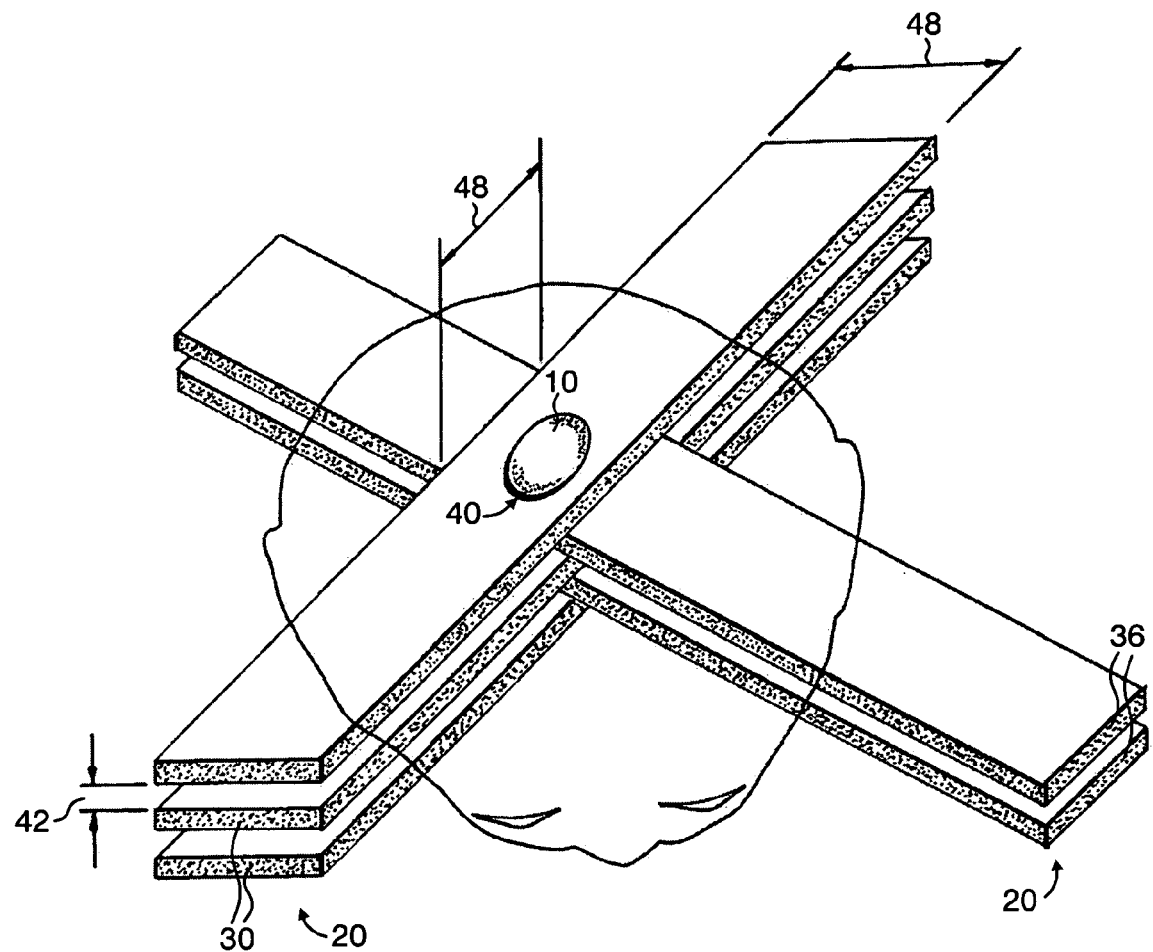
FIG. 1a is a schematic representation of an improved method of providing broad beam radiation to a brain tumor from two incident interlacing, i.e., interleaving, arrays of microbeams in accordance with an embodiment of the present invention, referred to as Bidirectional Interlaced Microbeam Radiation Therapy (BIMRT).

Referring to FIG. 1a, in one embodiment of the present invention, the therapeutic dose is delivered by irradiating the target tissue 10, a tumor, for example, with at least two arrays of microbeams, which interleave only within the target tissue 10.

An array 20 of microbeams includes at least two parallel, spatially distinct microbeams 30. The generally planar microbeams 30 of the array 20 have radiation planes 36, also referred to herein as beam planes 36 that are parallel to each other in the array. Each microbeam is separated from an adjacent microbeam in the array 20 by an inter-beam spacing 42.

Figure 1B:
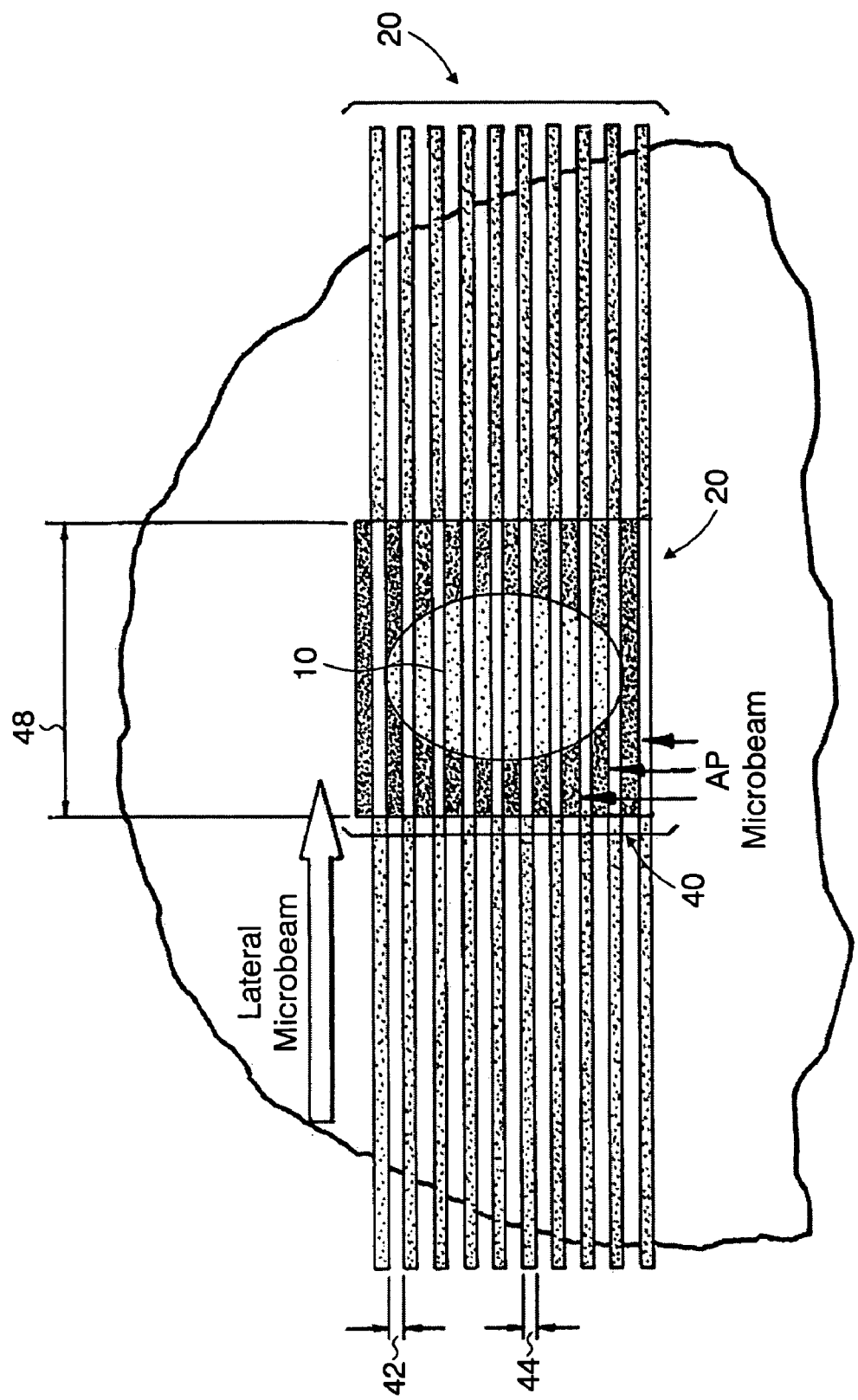
FIG. 1b is a schematic representation of the method of FIG. 1a from a side viewing angle.

The spacing 42 between adjacent beams 30 as used herein refers to the inter-beam spacing 42, rather than a center-to-center spacing, unless otherwise indicated. The inter-beam spacing 42 is generally measured from one edge or "wall" of a microbeam 30 to the adjacent wall of the adjacent microbeam as shown in FIG. 1a and FIG. 1b. The inter-beam spacing 42 is commonly measured approximately from the half-maximums of the adjacent microbeam intensity profiles.

The target tissue 10 refers to a volume of tissue encompassing the tumor, for example, and substantially no non-tumorous tissue.

Referring still to FIG. 1a, the method includes irradiating the target tissue 10 in a first irradiation direction with a first microbeam array. A second microbeam array is interleaved with the first to form a substantially continuous broad beam 40 of radiation only within the target tissue 10. The arrays 20 are preferably interleaved by translating either the subject or a source generating the array 20 in a plane perpendicular to the planes 36 of the microbeams, by at least a beam thickness 44, and angularly displacing, i.e., rotating, one array from another along a plane parallel to the irradiation paths and planes 36 of the microbeams between exposures of the target tissue 10 to the microbeam arrays 20. The axis of rotation about which the arrays 20 are rotated is preferably positioned through the center of the target volume 10, and perpendicular to the microbeam planes 36. In this way, the planes 36 of the array 20 in the first irradiation direction preferably remain substantially parallel to the planes 36 of the second array 20 after rotation. The target tissue 10 is also irradiated in the second irradiation direction, after the acts of translating and angularly displacing, so that the substantially continuous broad beam 40 or radiation is received only by the target tissue 10.

The microbeam arrays 20 are incident from different directions, so that the arrays 20 of radiation are interleaved substantially only within the target tissue 10, forming the substantially continuous broad beam substantially only within the target tissue 10.

In addition, the arrays 20 are non-intersecting arrays 20. In other words, the planes 36 of each array 20 do not cross or intersect the planes 36 of any other array 20 within the irradiated subject.

Preferably, two arrays of microbeams are angularly displaced by about ninety (90) degrees between exposures to the radiation.

The configuration of microbeams shown in FIG. 1a is referred to as a "bidirectional interlaced" geometry, and the use of two arrays of microbeams in this configuration to generate the continuous broad beam 40 substantially only within the target volume 10 is referred to as bidirectional interlaced MRT (BIMRT).

Referring also to FIG. 1b, in this geometry, the spacing 42 between the microbeams 30 in an array 20, also referred to herein (unless otherwise indicated) as the inter-beam spacing 42, is at least the thickness 44 of one microbeam. As described supra, the microplanar beams of each array have irradiation planes 36 that are substantially parallel to one another within the array, as shown in FIG. 1a.

In a preferred embodiment, the planes 36 of one array are also preferably substantially parallel to the planes 36 of each of the other non-intersecting arrays used to form the broad beam, so that all beam planes 36 of all arrays are parallel to one another. The at least two non-intersecting arrays, therefore, are preferably at least two parallel non-intersecting arrays.

As shown in FIG. 1a and FIG. 1b, the beams 30 preferably have a substantially rectangular cross-section with the thickness 44 corresponding to the shorter side of the rectangle. The parallel beam planes 36 extend over a width 48 of the rectangular cross-section that preferably equals or exceeds a length of the tumor 10 in that irradiation direction.

Referring again to FIG. 1b, most preferably, the inter-beam spacing 42 is substantially equal to the thickness 44 and one of the at least two non-intersecting arrays is shifted by one beam thickness 44 relative to another array between exposures. FIG. 1b is a representation of the same embodiment represented in FIG. 1a, but from a different angular view. In FIG. 1b, a profile of the array 20 for a first exposure to a microbeam array 20 is shown, clearly depicting the relationship between the beam thickness 44 and spacing 42 of the microbeams in the array 30. Upon rotating the array by 90 degrees, the direction of irradiation is into the plane of the paper, showing the width 48 completely covering the tumor in this direction. The array 20 is shifted by one beam thickness 44 in the vertical direction to tightly interleave the beams at the tumor 10, creating the substantially continuous broad beam 40 substantially only within the target tumor 10.

The arrays 20 may be rotated about an axis that is positioned through the center of the target volume 10 and that is perpendicular to the beam planes 36 and shifted or translated in a direction perpendicular to the beam planes 36, by any combination of rotating and translating the source and/or patient. For example, one source may be used to physically generate a microbeam array. The at least two non-intersecting arrays that interleave at the tumor are then produced by appropriate angular and linear displacement of the subject and/or the source.

Alternatively, two (or more, depending on the number of arrays) sources, e.g., bremsstrahlung sources, may be appropriately placed around the subject to independently generate the arrays from the appropriate directions, and in the appropriate planes.

In a preferred embodiment, the method of the present invention is performed using a system which includes a gantry on which two radiation sources, e.g., X-ray tubes, are positioned at 90° to each other for simultaneous exposure of the subject with interlaced (i.e., interleaved) arrays of beam planes. The system preferably includes tailored collimators for each angle to adjust the shape of the beam to the target volume's cross section. In addition, the system may include boluses to modulate the intensity in each direction at the level of the machine and across the field.

The dose to the subject exposed to microbeams may be described in terms of either an "in-beam" dose, a "valley" dose or, an integrated dose over a particular volume. The in-beam dose is defined herein as the dose within a single microplanar beam, whereas the valley dose is the dose between microbeams. The integrated dose is essentially the dose averaged over the in-beam and valley dose encompassed in a microbeam array within a volume of interest, e.g., within normal tissue and/or within the tumor.

As is well-known to one skilled in the art, a therapeutic dose is a dose of high energy electromagnetic radiation, typically measured in units of Gray ("Gy"), which is sufficient to effectively ablate or control a tumor.

A tolerance dose, or maximum tolerable dose, is the maximum dose that can be received by the subject without inducing unacceptable damage in normal tissue.

The concept of microbeam radiation therapy (MRT) and descriptions of microbeams and particular types of microbeam arrays are provided in U.S. Pat. No. 5,339,347 to Slatkin et al., which is incorporated herein by reference. The goal of microbeam radiation therapy is the same as the goal of conventional therapy: that is, to maximize the therapeutic index, which is defined as the ratio of the maximum dose tolerated by the subject beyond which unacceptable levels of normal tissue toxicity would occur, to the minimal dose required for effective tumor ablation or control.

It has been established that capillary blood vessels are involved in the normal-tissue sparing effect of microbeams. It is also well-established that regions of the capillary blood vessels damaged in the direct paths of microbeams are regenerated by supportive cells surviving in the valley areas, i.e., in the sufficiently unirradiated or minimally irradiated microscopic zones between the microbeams of a microbeam array. In contrast, the thickness of the broad beam of conventional radiation therapy (typically on the order of tens of millimeters) is too large to allow the necessary repair to occur from the surviving cells. Because the capillary blood vessels constitute the basic infrastructure of bodily tissue, their survival is the most important factor in the recovery of the normal tissue from high energy radiation.

As a result, though MRT seeks to accomplish the same goal as conventional therapy, because of the ability of normal tissue to recover from radiation-induced damage from microbeams, it is fundamentally different from and offers superior advantages over conventional broad beam radiation therapy. For example, typical tolerance doses of the central nervous system (CNS), e.g., the brain and spinal cord, using conventional dose fractionated broad beam therapy are on the order of about 10–20 Gy per fraction dose for a total of about 60 Gy, i.e., in several single-fraction doses administered over several sessions separated by some time interval. In MRT, for example, for a single array with very narrow beams of 20–90 microns (μm) thickness, the typical in-beam dose tolerances are much greater. For example, single-fraction in-beam doses of up to about 500 Gy can be tolerated by the CNS.

A microbeam of the present invention is preferably defined, therefore, as a high energy electromagnetic radiation beam having a thickness sufficiently small to prevent substantial radiation-induced damage to normal in-beam tissue, i.e., having a thickness small enough in size relative to the inter-beam spacing to allow regeneration of normal tissue in the path of a radiation beam. The optimal thickness of the microbeam will subsequently depend upon the capacity of the particular tissue surrounding a beam path to support the recovery of the tissue injured by the beam, but is also dependent on the spacing between adjacent microbeams used in a microbeam array.

In a preferred embodiment, the thickness of a microbeam in an array used in BIMRT is greater than or equal to 500 μm and less than or equal to about 1000 μm. Though the beam width must be thin enough to retain the microbeams' normal tissue-sparing characteristics, providing a wider beam (over 500 µm) advantageously reduces sensitivity to mechanical misalignments and favors the use of bremsstrahlung X-rays from industrial X-ray generators.

In another embodiment of the method of the present invention, microbeams are provided which include a thickness substantially in a range of greater than or equal to about 10 µm and less than or equal to about 1000 µm.

In still another embodiment, microbeams are provided which include a thickness substantially in a range of greater than or equal to about 20 µm and less than or equal to about 100 µm.

In yet another embodiment, microbeams are provided which include a thickness substantially greater than or equal to about 10 µm.

In a further embodiment, microbeams are provided which include a thickness substantially less than or equal to about 500 µm.

In still another embodiment, microbeams are provided which include a thickness substantially less than or equal to about one millimeter.

The microbeam of the present invention is preferably substantially collimated at least in one plane, exhibiting minimal divergence in the at least one plane. In addition, the microbeam preferably includes substantially sharp, well-defined edges at least at the edges bordering adjacent microbeams in the array, along the thickness of the microbeam.

A major attribute of the bidirectional interlaced microbeam method is that the broad-beam irradiation zone it produces at the target volume has very sharp edges, so that the dose at the edges of the target volume falls very rapidly. The sharpness of this dose fall off is measured as the distance when moving away from the target volume where the dose falls from 90% of its value to 10%. For interlaced microbeams, this distance can be 10–30 µm, which is considered to be extremely short compared to those in all other radiotherapy methods, including the methods using MeV X-rays, protons, neutrons, and heavy ions for which the edge, as defined above, is at least close to 1 mm, and often up to 3 mm. Using interlaced microbeams, beyond this edge of 10–30 µm there is no broad beam, but only microbeams, which are not damaging the normal tissue. During treatment planning, this sharp edge will be put between the tumor and the sensitive normal tissue one desires to spare. In this way, the sensitive normal tissue receives almost no damage (because it is exposed to a single array of microbeams), while the tumor gets the full dose of broad beams.

Ocular melanoma is one example of a clinical radiotherapy application in which a tumor is located within 1–2 mm of a sensitive organ (in this case the eye as a whole, or certain parts of it). Proton therapy is the current preferred method of treatment ocular melanoma because it has a relatively sharper dose fall off compared to high energy X-rays. However, even with proton therapy the dose falloff is many hundreds of µm. The sharp fall off of 10–30 µm makes BIMRT an ideal choice, therefore, for the treatment of ocular melanoma. Damage to tissue from incident radiation occurs only at the tumor, where the arrays are interleaved to form an effectively continuous broad beam of radiation. Outside the tumor, the non-intersecting arrays of the present invention do not interleave to form broad beam, but remain discretely spaced, and thus may cross the most sensitive tissues, such as the retina, with substantially no adverse consequences.

The irradiated target volume in bidirectional-interlaced microbeams does not have to be limited in its shape to be a rectangular box. The beam from each direction may be collimated in a tailored way to conform to the cross section of the target volume when viewing the target from that particular angle. The shape, therefore, can be irregular. Furthermore, the depth of the dose penetration for each irradiation angle can be modulated across the field by using tailored boluses for irradiations from each direction.

The microbeam array of the present invention includes at least two spatially discrete and substantially parallel microplanar beams, which are used to create a broad beam effect within the target tumor. Preferably, the microbeam array includes substantially equally-spaced microplanar beams.

Alternatively, instead of microplanar beams, the array may be a pencil beam with a circular, square, or otherwise substantially radially symmetrical cross-section.

Irradiation with arrays from different incident angles may use collimators and boluses of different shapes for non-uniform dose delivery to the subject, as in conventional radiation therapy.

Preferably, several microbeams are produced simultaneously in a microbeam array, using a collimator having any of various designs known in the art. Such collimators have multiple radiation transmissive apertures allowing an array of regularly spaced microbeams to be produced simultaneously.

The method of the present invention may be implemented using any source of high energy electromagnetic radiation having a fluence rate high enough to generate the required therapeutic dose in an array of microbeams, such as X-rays or gamma rays.

In the preferred embodiment of the method of the present invention, the high energy electromagnetic radiation includes X-ray radiation.

The appropriate X-ray radiation may be generated by filtering radiation produced by an X-ray source, for example, a high energy synchrotron or an X-ray tube. The fluence rate of the source used to implement the method of the present invention is preferably high, so that exposure times are sufficiently short, reducing the possibility of smearing the microbeam dose pattern produced in the tissue.

One possible source of X-rays is a wiggler insertion device in a so-called "beamline" of an electron storage ring of an X-ray synchrotron. An exemplary beam source is the superconducting wiggler insertion device of the X17B beamline of the National Synchrotron Light Source at Brookhaven National Laboratory, Upton, N.Y. A conventional "planar" wiggler uses periodic transverse magnetic fields to produce a beam of rectangular cross-section, typically having a horizontal to vertical beam opening angle ratio on the order of 50:1. In an alternative embodiment, the radiation beam is obtained from a "helical" wiggler, a configuration capable of producing a substantially less anisotropic beam.

In a preferred embodiment, the source will be a bremsstrahlung industrial X-ray generator. The bremsstrahlung X-ray source may include a high-throughput rotating anode X-ray tube operating at a very high voltage (about 150 kV-peak or higher) and a very high current (100 mA or higher). The beam is preferably filtered with copper or heavier elements to eliminate the low end of the energy spectrum, thus producing a higher mean spectral energy.

It is advantageous to keep the edge of each microbeam dose sharp, to lower the valley dose in the normal tissue. The in-beam dose fall off depends on the so-called "beam penumbra," which depends on the source focal spot size, among other factors. For these reasons, the focal spot size of the X-ray source should be minimized, especially for the bremsstrahlung source.

The X-ray microbeam array is preferably generated using a multislit collimator, well-known to those skilled in the art, positioned in the path of the beam generated by the X-ray source and in front of the subject. The multislit collimator is typically made of a heavy metal such as tungsten or lead. The collimator segments the source beam, which is generally a fan-shaped beam of about a few millimeters height, into regularly spaced parallel microplanar beams or microbeams.

In the method of the present invention, the preferred energy range of the photon spectrum from an X-ray source producing the therapeutic dose is about 50 keV to about 300 keV. Preferably, a filtered X-ray source is used, which has a peak energy within the range of about 50 keV to about 300 keV. Most preferably, the photon energy of the filtered source peaks within the range of about 120 keV to about 300 keV.

In one embodiment, the high energy electromagnetic radiation includes a photon energy less than or equal to about 300 keV.

In another embodiment, the high energy electromagnetic radiation includes a photon energy greater than or equal to about 50 keV.

The therapeutic dose required to effectively control and substantially eradicate the target tissue can be delivered in a single session, using any of the interlaced MRT (two or more angularly displaced arrays) methods described herein.

Alternately, the therapeutic dose may be administered over several sessions separated by some time interval in so-called "dose fractionations."

In a preferred embodiment, the therapeutic dose is delivered by administering the dose over more than one session in dose fractionations, where a sum of the dose at the tumor is substantially equal to the desired therapeutic dose. The sessions are separated over a time interval. The time interval is chosen to allow the first recovery phase of the microvasculature from the microbeams to occur. The time interval may be within a range of about three hours to about five days.

In interlaced MRT, the ideal dose fractionation regimen is only two fractions, preferably 1–5 days apart. Each dose fraction session includes the administration of the two (BIMRT) or more interlaced arrays. In a second session, the plane of the two or more microplanar arrays is rotated 90°, so that a rotation axis of the gantry in the second session will be perpendicular to that of the first session. In this way, the same normal tissue is not irradiated again in the same microplanar beam direction in subsequent sessions.

In one embodiment, the sessions are separated by a time interval within a range of about 12 hours to about 30 hours.

In another embodiment, the sessions are separated by a time interval of greater than or equal to about 12 hours.

In yet another embodiment, the sessions are separated by a time interval of less than or equal to about four days.

A major problem with the existing methods of radiation therapy is that if the tumor recurs and a new administration of radiation therapy is needed, the dose of the new treatment is limited to a maximum accumulative dose. In other words, the tissue, particularly the central nervous system (CNS), that is, the brain and the spinal cord, "remember" the damage from the earlier radiation therapy treatments. MRT doses to the normal tissue will not be subject to such strict limitation because the tissue damage and the tissue recovery processes in MRT are different (and more gentle) from that of the conventional radiation therapy.

In the method of the present invention, therefore, retreatment of the tumor to control recurring tumors may advantageously ensue after a separation of from six months to about five years.

A therapeutic dose, therefore, may be administered in any of the interleaved MRT geometries of the present invention with preferably 500 μm to 700 μm thick beams, in fractionated doses, with the total therapeutic dose delivered to the target tissue being preferably in a range from about 40 to about 80 Gy.

The therapy may be administered in up to about six exposures, with appropriate time delays between them. Most preferably, only two sessions are administered.

This "dose fractionation" has the following benefits. First, it requires smaller dose in each exposure, which has the following benefits: a) it lowers the risk of radiation damage to the parenchymal cells and tissues; b) it requires shorter exposure times; and c) it reduces the problem of radiation leakage between the individual microbeams stemming from X-ray scatter in large irradiation volumes and large subject sizes. Second, the method takes advantage of the fast recovery of the normal tissue from unidirectional microbeam irradiation to minimize the radiation damage from the previous exposures.

Figure 2A:
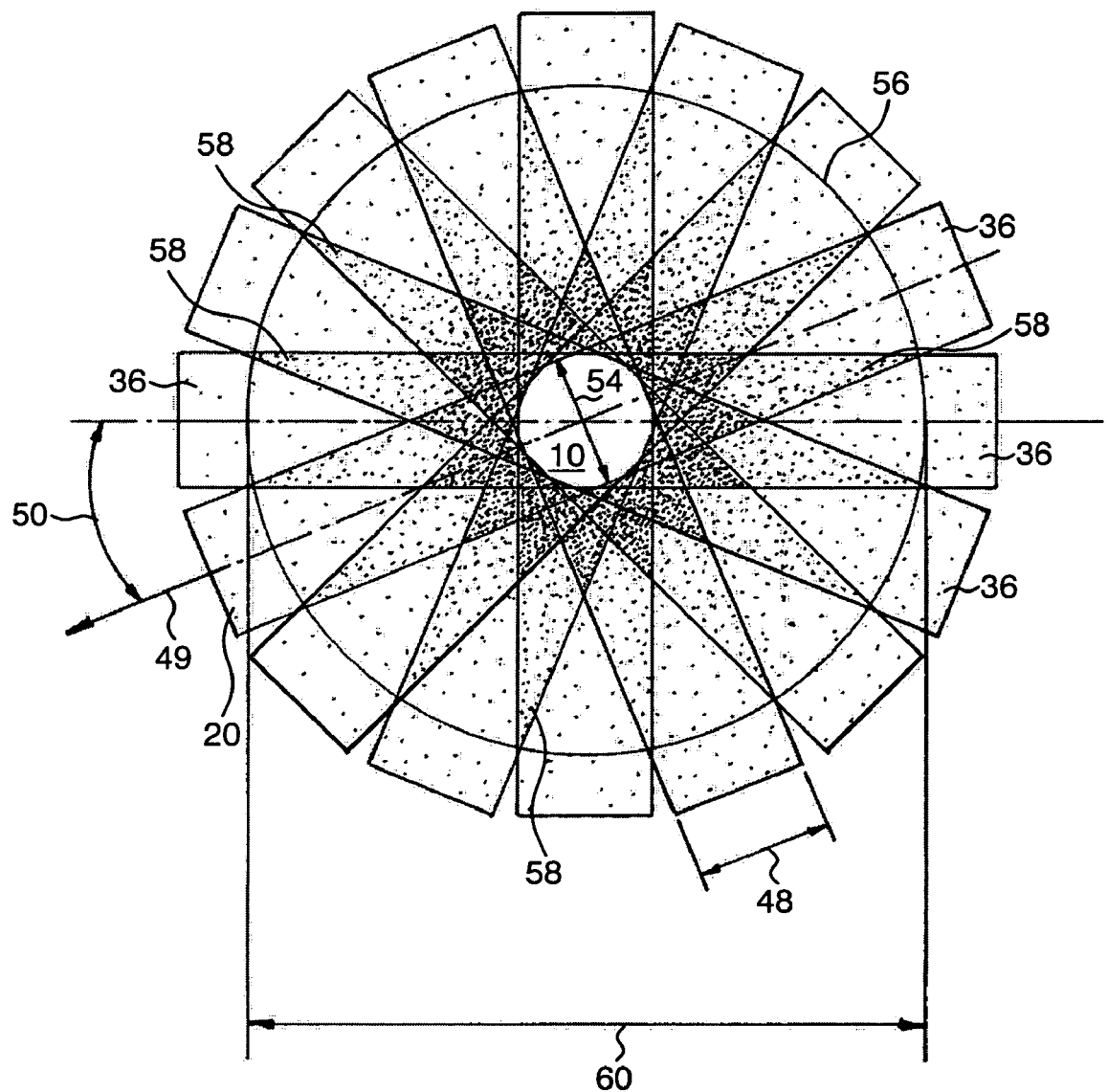
FIG. 2a is a schematic top-view representation of an improved method of providing broad beam radiation to a tumor in accordance with another embodiment of the present invention, referred to as Multidirectional Interlaced Microbeam Radiation Therapy (MIMRT).

Referring to FIG. 2a, another embodiment of the method of the present invention for performing radiation therapy on a subject includes delivering a therapeutic dose of high energy electromagnetic radiation to a target tissue 10 with a substantially continuous broad beam of radiation, using multidirectional interlaced MRT (MIMRT). The therapeutic dose is delivered by irradiating the target tissue 10 with a microbeam array 20 directed along a path 49; angularly displacing or rotating the subject or source by a discrete angle 50 about an axis that goes through the center of the target and that is perpendicular to the microbeam planes 36 (i.e., in the plane of the paper in FIG. 2a); and translating the subject by at least a beam thickness in a plane substantially perpendicular to the path (into the plane of the paper in FIG. 2a) as in BIMRT, and repeating the steps of irradiating the target tissue 10, angularly displacing and translating multiple times using one of a continuous scanning mode and a stepwise step-and-shoot mode.

Figure 2B:
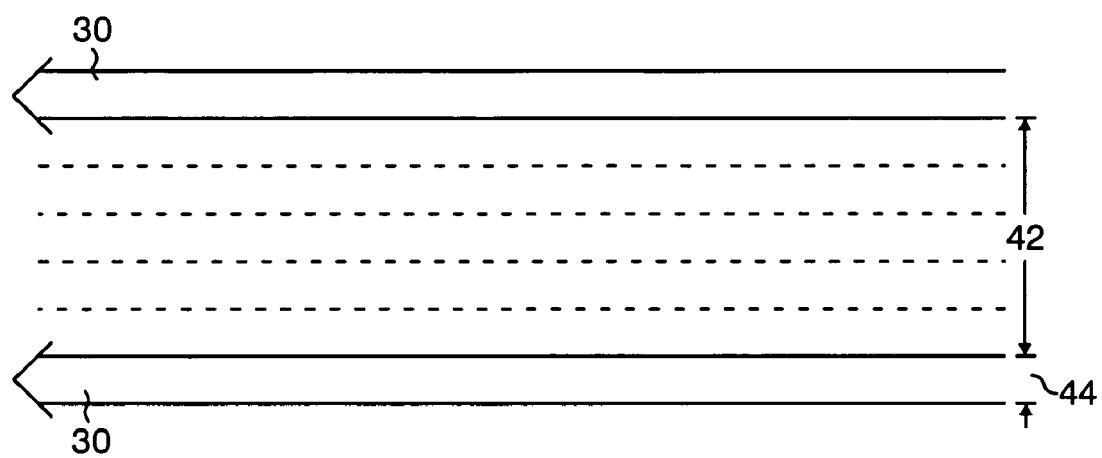

Referring also to FIG. 2b, the beam spacing 42 between microbeams 30 in the microbeam array 20 is preferably substantially equal to the distance required to interleave the multiple non-intersecting arrays and produce a substantially continuous broad beam of radiation within the target volume 10.

In this method, the subject is irradiated from n angles (n>2) preferably over the entire angular space around the tumor (360°) for the purpose of spreading the entrance dose over a larger region of the body of the subject, thus reducing the dose in each microbeam array.

In the preferred embodiment, each irradiation is performed after angularly displacing the microbeam array 20 preferably by an angle substantially equal to 360/n and translating as in the BIMRT case by a distance equal to the beam thickness 44. As shown in FIG. 2b, the inter-beam spacing 42 (distance between adjacent microbeam walls in the array), therefore, is preferably (n−1) times the thickness 44 of an individual microbeam in the array. In FIG. 2a, for example, n=16, and the angle between exposures is 3600°/16=22.5°. The inter-beam spacing is preferably (n−1) or 15 times the beam thickness. Similarly, in FIG. 2b, n=6, the inter-beam spacing 42 is 5 times the thickness 44, and the angle between exposures is 60°. The method includes performing n irradiations covering a 360° angular space around the tumor, to form a substantially continuous broad beam substantially within the target volume 10.

As in the bidirectional interlaced method, the width 48 of the entire array incident from each direction is preferably substantially equal to the target width 54 of the target volume 10 as viewed from that direction.

To optimally dilute the entrance dose to the subject using MIMRT, n is preferably chosen so that adjacent arrays would touch each other at the edge 56 of the subject (e.g., patient), if there were no perpendicular shifting. As shown in FIG. 2a, this method produces interlacing, i.e., interleaving, of the microbeams at the target volume 10 to produce a substantially continuous broad beam within the target volume, as well as partial interleaving (two beam thicknesses) of adjacent microbeams at two triangular regions 58 before and after the target.

Upon completion of the n irradiations from all angles (360° around the subject), the dose produced in the target volume 10 will be a solid-beam dose. Referring still to FIG. 2a, in the hypothetical example of a cylindrical tumor 10 of diameter d 54 at the center of a cylindrical subject 56 of diameter D 60, the formula for calculating n for optimal dilution is: $n=\pi D/d$. Besides diluting the entrance dose, this irradiation method also has the advantage of increasing the inter-beam spacing 42, which equals n times the thickness 44, as opposed to the inter-beam spacing being equal to the thickness, as is the case in BIMRT. This larger inter-beam spacing 42 reduces the scattered dose between microplanar beams in each array 20 (i.e., the "valley" dose). Because the normal tissue is subjected to only non-interleaving microbeam arrays, it is essential to keep the valley dose low to allow the tissue to survive in the valley region within the normal tissue.

The multidirectional interlaced microbeam method is suitable more for smaller ratio of target size/subject size; i.e., it is most useful when the target volume is quite small compared to the size of the subject. Because the triangular areas produced by the interleaving of the adjacent arrays (having twice the beam thickness) may be large, the beam thickness must be chosen so that there is still a beam-sparing effect for an array with a beam thickness equal to twice that in the individual arrays.

The method of the present invention for performing radiation therapy on a subject may also include enhancing the therapeutic dose and broad beam effect by providing a concentration of a radiation contrast agent to the target tissue.

In one embodiment, a contrast agent is administered to the tumor, by any means known to those skilled in the art, before applying any of the methods of interlaced MRT, such as BIMRT or MIMRT. The contrast agent is chosen to enhance the in-beam absorption of the incident interleaved radiation substantially only within the target tissue. The optimum contrast agent for optimum absorption will depend, therefore, on the incident radiation spectrum of the microbeams.

The contrast agents used as radiation absorption enhancers preferred for use with the interlaced microbeam geometries of the present invention include heavy elements, preferably of atomic number larger than 70.

In one embodiment, the contrast agent includes a material characterized by a K-edge of at least 65 keV, such as tungsten (69.525 keV) or gold (80.725 keV). In a preferred embodiment, the contrast agent includes gold.

The contrast agent using heavy elements is used in conjunction with interlaced microbeams to raise the in-beam dose in the tumor more than the valley dose, and thus effectively to reduce the valley. Because in interlaced microbeams the normal tissue is the only part of the body that receives microbeams (the tumor receives broad beam produced by the interlaced microbeams), the effective lowering of the valley dose relative to the in-beam dose makes the microbeam safer to the normal tissue. The low end of the incident beam energy spectrum is preferably only slightly higher than the K-edges of both tungsten and gold (69.525 keV and 80.725 keV, respectively) for optimum dose deposition within the in-beam tissue. The spectrum of the radiation scattered into the valleys between the microbeams will be shifted below the K-edges of these elements, where the attenuation coefficient is very low. The dose deposition in the valleys, therefore, is much lower than that in the direct beam path.

Figure 3:
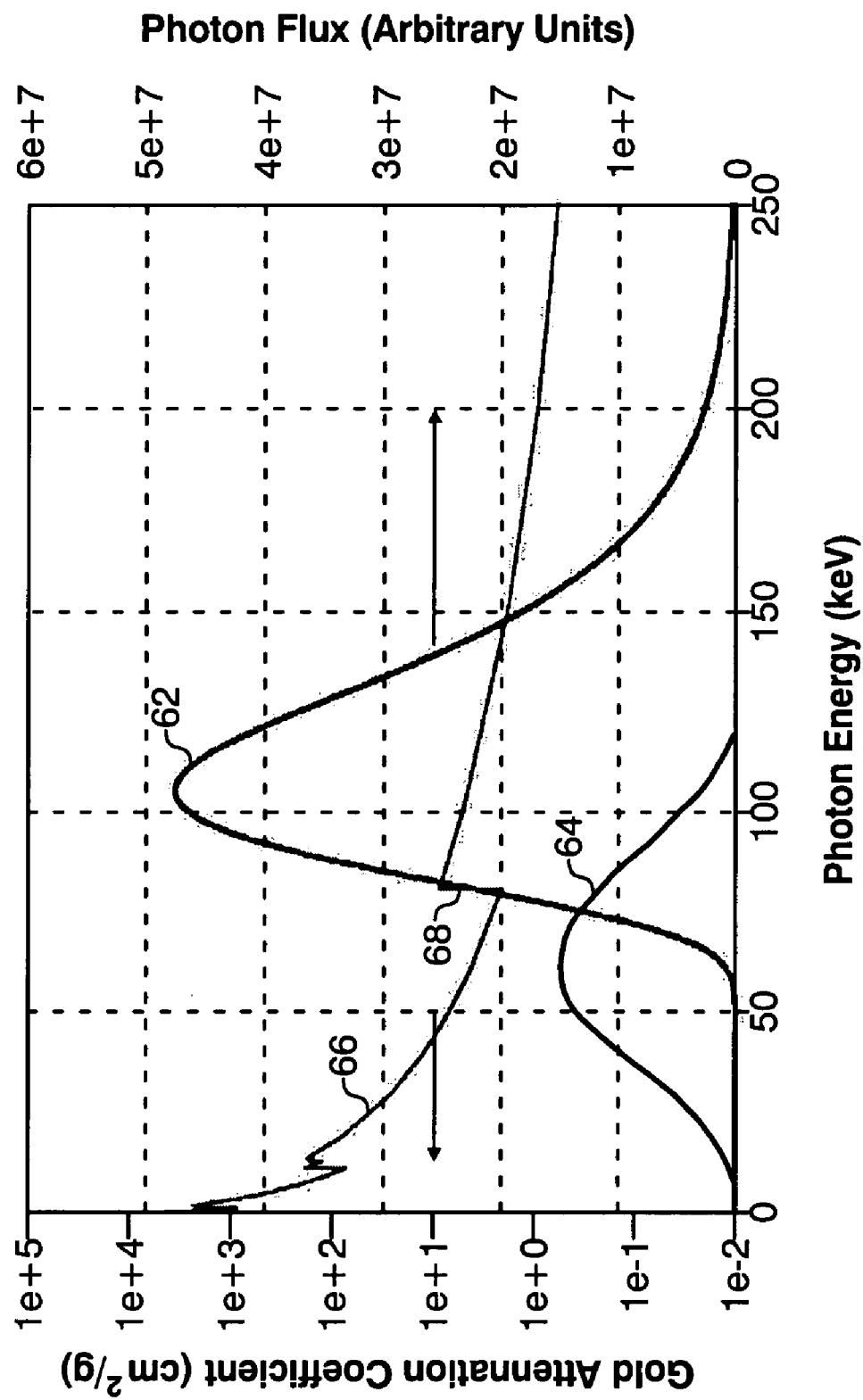
FIG. 3 is a plot of incident and scattered radiation spectra for a radiation contrast agent, gold, of the present invention, superimposed over a plot of the attenuation coefficient of gold.

FIG. 3 shows an incident X-ray spectrum 62 from a filtered X-ray source and the scattered spectrum 64 of radiation from a contrast agent including gold. The spectra are superimposed on the plot of the attenuation coefficient of gold 66. The lower end of the incident spectrum 62 overlaps with the K-edge 68 of 80.725 keV, so that absorption is enhanced for that part of the spectrum 64 of in-beam dose of gold radiation falling just above the K-edge 68.

In a preferred embodiment, the contrast agents of the present invention are administered in the form of metal particles, or nanoparticles. Metal nanoparticles provide a means of achieving the desired effect of enhancing radiation absorption, without the tissue-toxicity that would be incurred using the amount of metal ions, for example, that would be needed to produce the desired useful effect.

The metal nanoparticles of the present invention may include gold, tungsten, and other metals having an atomic number above 70, which can be administered safely to the subject. A metal nanoparticle may be formed of one or more different types of metals.

The metal nanoparticles of the present invention have a central core of solid metal in the zero oxidation state. This core can be of various shapes, including spherical, ovoid, star-like. The core can be from about 0.5 nanometers to about 3 micrometers in size.

This metal core is then surrounded by an organic shell that is either covalently bonded to surface metal atoms, or adsorbed by non-covalent bonds to the metal surface. This shell contributes strongly to the in vivo properties of biodistribution, clearance, and toxicity, and the shell can be hydrophilic, hydrophobic, positively charged, negatively charged, polar, non-polar, or mixtures of these entities. The metal surface usually has room to attach multiple organic ligands, and the ligand shell can therefore be homogeneous or contain different ligands.

The organic shell can also be an antibody, drug, or other compound for directing the particle to a target site, or used to incorporate biological binding or activity to the particle. The antibody, drug, or other compound may also be linked to a preexisting organic shell. One skilled in the art will be able to choose the appropriate metal nanoparticle that confers the desired properties for use with the interleaved MRT methods of the present invention.

The large gain in therapeutic efficacy that can be achieved by combining the interlaced MRT method with the administration of heavy-element contrast agents (such as tungsten and gold) to the subject, can be best implemented with the use of gold nanoparticles from Nanoprobes, Inc, Yaphank, N.Y. These nanoparticles, which can be administered both in a physiologically targeted and non-targeted way, have already been proven to be safe on laboratory animals and have produced remarkable results as a contrast agent for both X-ray imaging, including computed tomography, and for radiation therapy, as discussed in Hainfeld, J. F., Slatkin, D. N., Smilowitz, H. M., "The Use of Gold Nanoparticles to Enhance Radiotherapy in Mice," Phys. Med. Biol. 49(18): N309–N315 (2004), which is incorporated herein by reference.

The great synergy between these two methodologies (MRT, particularly BIMRT and MIMRT, on the one hand and gold nanoparticles on the other hand) can be summarized as follows: a) gold nanoparticles are safe to the subject up to very high concentrations; b) the nanoparticles can be administered using physiologically targeted and non-targeted methods; c) they can be produced at different sizes (by adjusting the manufacturing process) so that they will be optimally up-taken by the tumor (by virtue of having the right size diameter to leak through the tumor's microvasculature) while staying inside the microvasculature of the normal tissue; d) gold nanoparticles stop X-rays at the highest cross section when used with the X-ray microbeams preferred for use with BIMRT and MIMRT (i.e., one with median beam energy of 100 keV to 140 keV); and, e) in the normal tissue surrounding the tumor, which receives only non-interlaced microbeam dose, the addition of gold nanoparticles reduces the valley dose relative to the peak dose (i.e., in-beam dose), or at least does not increase it. The nanoparticles, therefore, enhance the safety of the method for normal tissue.

In other words, for a given incident dose of the beam, the tumor dose will be increased by tens of percent while the microbeam valley dose in the normal tissue is increased by just a few percent. This small increase can be reduced to nothing by reducing the incident dose, accordingly.

In one embodiment of the method of the present invention, the contrast agent includes gold nanoparticles averaging about 1.9 nanometers in diameter. When this contrast agent was administered to tumors in mice, irradiation of the tumors with interlaced microbeams according to the present invention were found to produce improved survival rates over the interlaced microbeam method used without the contrast agent (see Example infra).

In another method of the present invention for performing radiation therapy on a subject, a therapeutic dose of radiation is delivered substantially only to a target tissue by generating an in-effect broad beam radiation dose substantially only within the target tissue, using at least one microbeam array and a radiation scattering agent administered to the tumor.

The radiation scattering agent of the present invention is a contrast agent characterized by a lower K-edge value, which acts as an X-ray scatterer, rather than an absorption enchancer, of incident in-beam radiation. In this embodiment, the therapeutic dose is preferably administered using non-interlaced microbeam array(s), including a single unidirectional microbeam array or cross-fired microbeam arrays that intersect substantially only within the target, as describe in the Slatkin, et al. patent, which has been incorporated herein by reference. The contrast agent preferably scatters a substantial amount of the incident microbeam radiation substantially sideways to the individual microbeam planes 36 inside the incident microplanar array, thus raising the valley dose relative to the peak dose and creating a continuous broad beam effect substantially only within the target volume.

The radiation scattering agent used in this method to scatter radiation within the tumor preferably includes lighter contrast elements with atomic numbers below 70.

In one embodiment, the radiation scattering agent includes at least one of iodine and gadolinium.

For both synchrotron beam and bremsstrahlung beams, which have energy spectra of about 120 keV median energy in the incident beam (full width at half maximum of 60 keV), the use of contrast media based on gadolinium (Gd) or iodine (I) will raise the valley dose compared to the peak dose. This is because the incident beam energy is much higher than the K-edges of both gadolinium and iodine (50.24 and 33.17 keV, respectively), while the valley dose, which is made of scattered X-rays, has lower energy and therefore its energy spectrum is closer to the K-edges of Gd and I. Because there will be more contrast media in the tumor than in the normal tissue, the net effect of raising the valley dose preferentially in the tumor causes preferential damage to the tumor because the valley dose acts as a background of broad beam.

Figure 4:
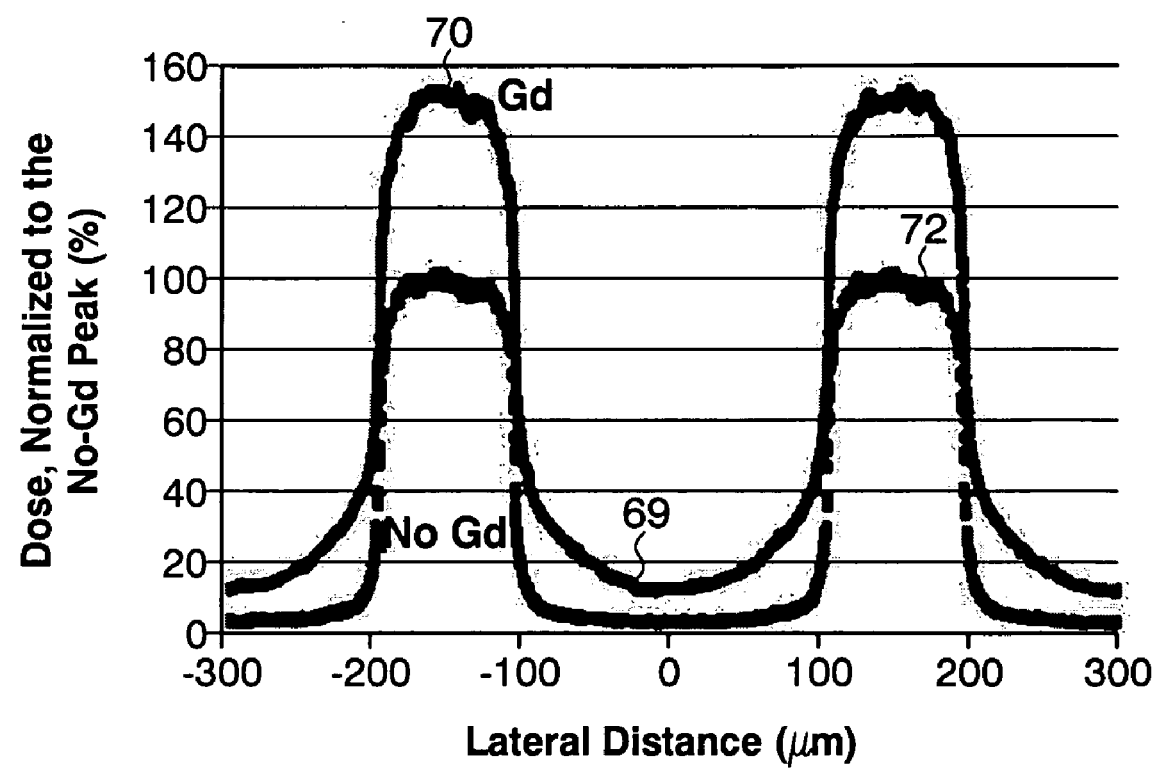
FIG. 4 is a graphical representation of the broad beam effect of a method of the present invention (a raising of the valley dose between microbeams in the tumor), which includes providing a concentration of a radiation scattering agent to the tumor. In this simulation, the tumor is a brain tumor in a rat.

FIG. 4 is a plot of dose simulation in a rat head phantom for a single unidirectional, parallel microbeam array, showing the effect of a scattering agent on the valley dose 69 between microbeams in an array. The microbeam width is approximately 90 μm and the inter-beam spacing is about 210 μm (on-center spacing of 300 μm). The valley dose 69 is significantly raised, but substantially only within the target tissue. The use of a scattering agent in the target tissue, therefore, preferably produces an effective broad beam effect substantially only within the target tissue.

FIG. 4 shows plots of the peak dose (in-beam dose) with 70 and without gadolinium 72 in a rat head phantom with 10 mg Gd/ml tumor uptake of gadolinium contrast media in the form used for magnetic resonance imaging (MRI) (e.g., gadobutrol, a neutral complex consisting of gadolinium (III)). The phantom was a 4 cm diameter water sphere inside 0.6 mm thick skull, with a 5-mm diameter tumor in its center. The microbeam array was 10 mm×10 mm. When Gd was added the peak dose increased 1.5-fold, while the valley 69 was raised 3.0-fold, i.e., a net valley rise of two-fold in tumor.

Figure 5:
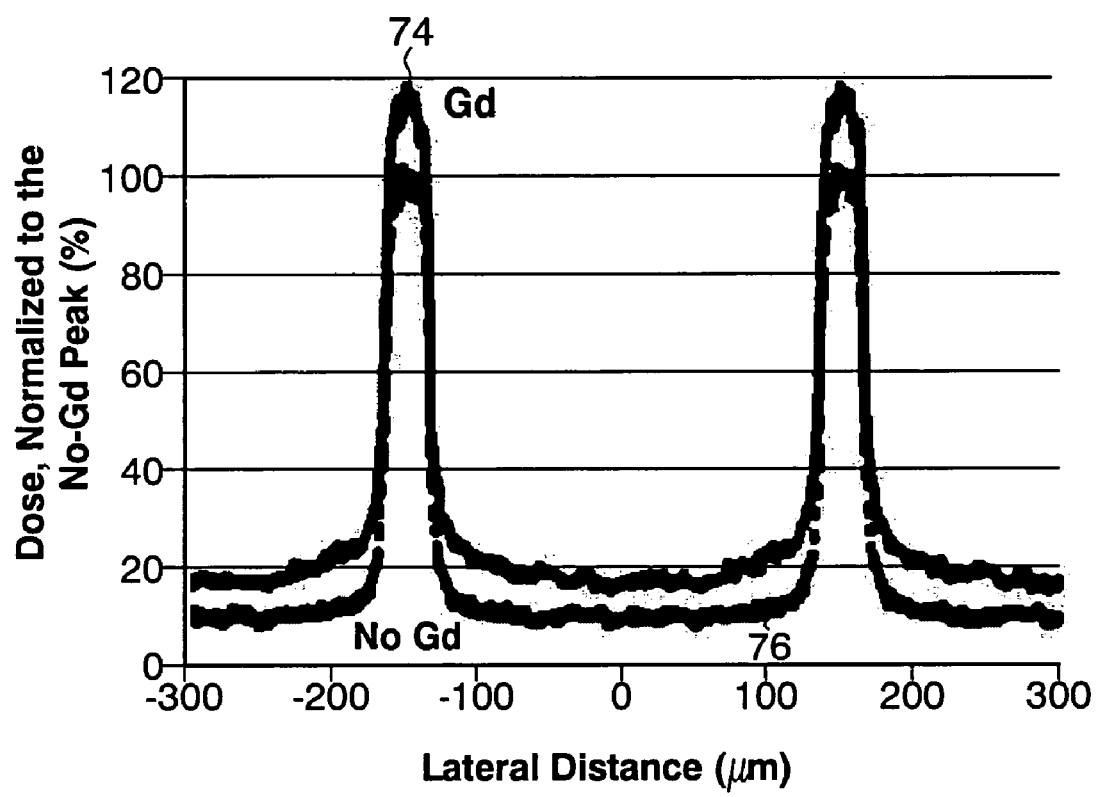
FIG. 5 is a graphical representation of a simulation of a method of the present invention showing the effect of providing a concentration of a radiation scattering agent to a human brain tumor irradiated with a single array of parallel microbeams.

FIG. 5 shows dose simulations with 74 and without gadolinium 76 in a human head phantom with 5 mg Gd/ml tumor uptake of gadolinium. The phantom was a 16 cm diameter water sphere inside 6 mm thick skull, with a 50 mm diameter tumor in its center. The unidirectional microbeam array had a 60 mm×60 mm cross-section, an approximate beam with of 30 μm, and approximate inter-beam spacing of 270 μm (equivalent to 300 μm center-to-center spacing). When Gd was added the peak dose increased 1.15-fold, while the valley was raised by 1.7-fold, i.e., a net valley rise of about 50% in tumor.

The scattering agent may be used with any of the MRT methods of the present invention. Preferably, a single microbeam array is used to irradiate the tumor injected with the scattering agent. The spacing between microbeams in the microbeam array is preferably as small as possible to optimize the valley dose within the target tissue, but just large enough to allow recovery of irradiated normal tissue outside the target tumor.

Figure 6:
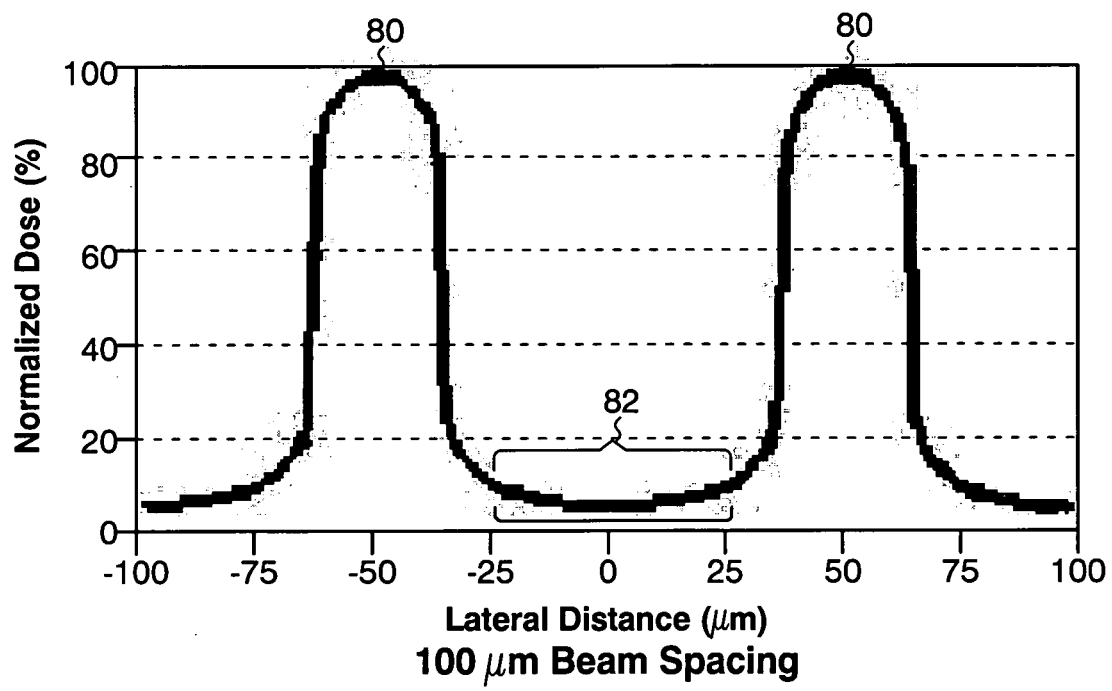
FIG. 6 is a plot of relative peak to valley dose within a target tissue for a microbeam array with about 27 micron (μm) beam thickness and about 73 μm inter-beam spacing (100 μm on-center beam spacing), without a scattering agent.
Figure 7:
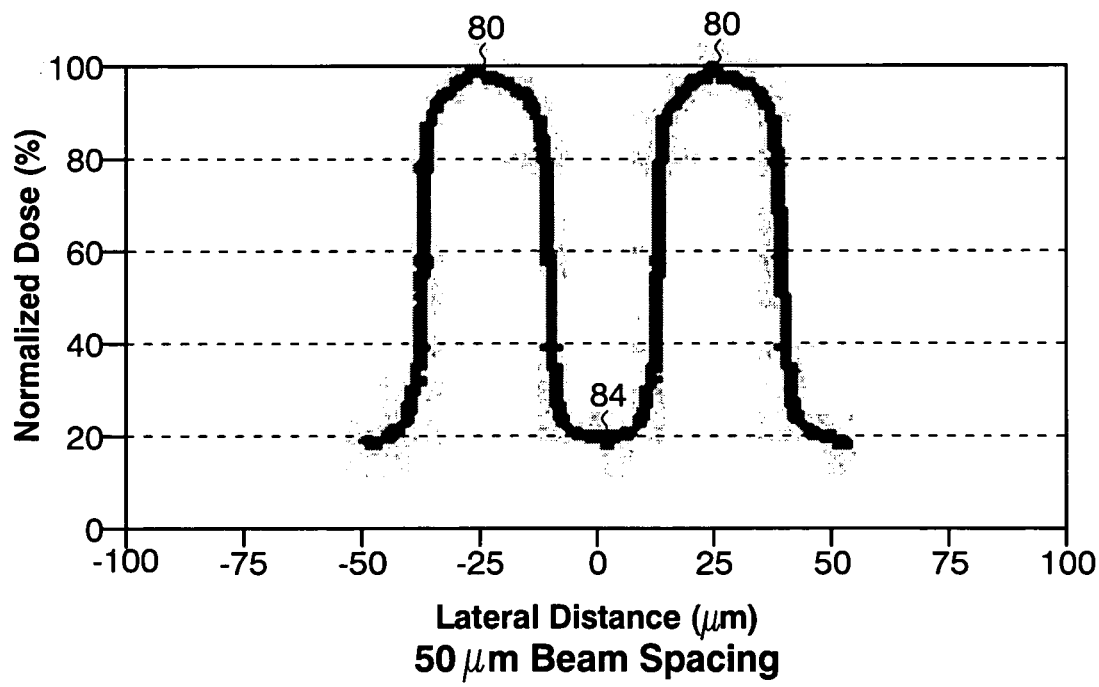
FIG. 7 is a plot of relative peak to valley dose, without a scattering agent, for a single microbeam array with the same beam thickness as FIG. 6, but with reduced inter-beam spacing of about 23 μm (50 μm on-center beam spacing) showing enhanced valley dose.

FIG. 6 is a plot of the dose distribution, including the relative peak 80 and valley dose 82 within a target tissue for a unidirectional microbeam array with about a 27 μm beam thickness and about a 75 μm beam spacing, without a scattering agent. Without yet introducing the scattering agent, one can see from FIG. 7 that simply reducing the spacing from 75 μm to about 25 μm increases the valley dose from about 5% 82 to about 20% 84, which helps create a broad beam effect. Therefore, by utilizing both a smaller beam spacing and an appropriate scattering agent injected to the tumor, an enhanced broad beam effect is expected.

To achieve the broad beam effect, a concentration of the scattering agent must be great enough to provide adequate scattering to provide the therapeutic dose to the valley zones, but smaller than the amount that is harmful to the patient.

Figure 8:
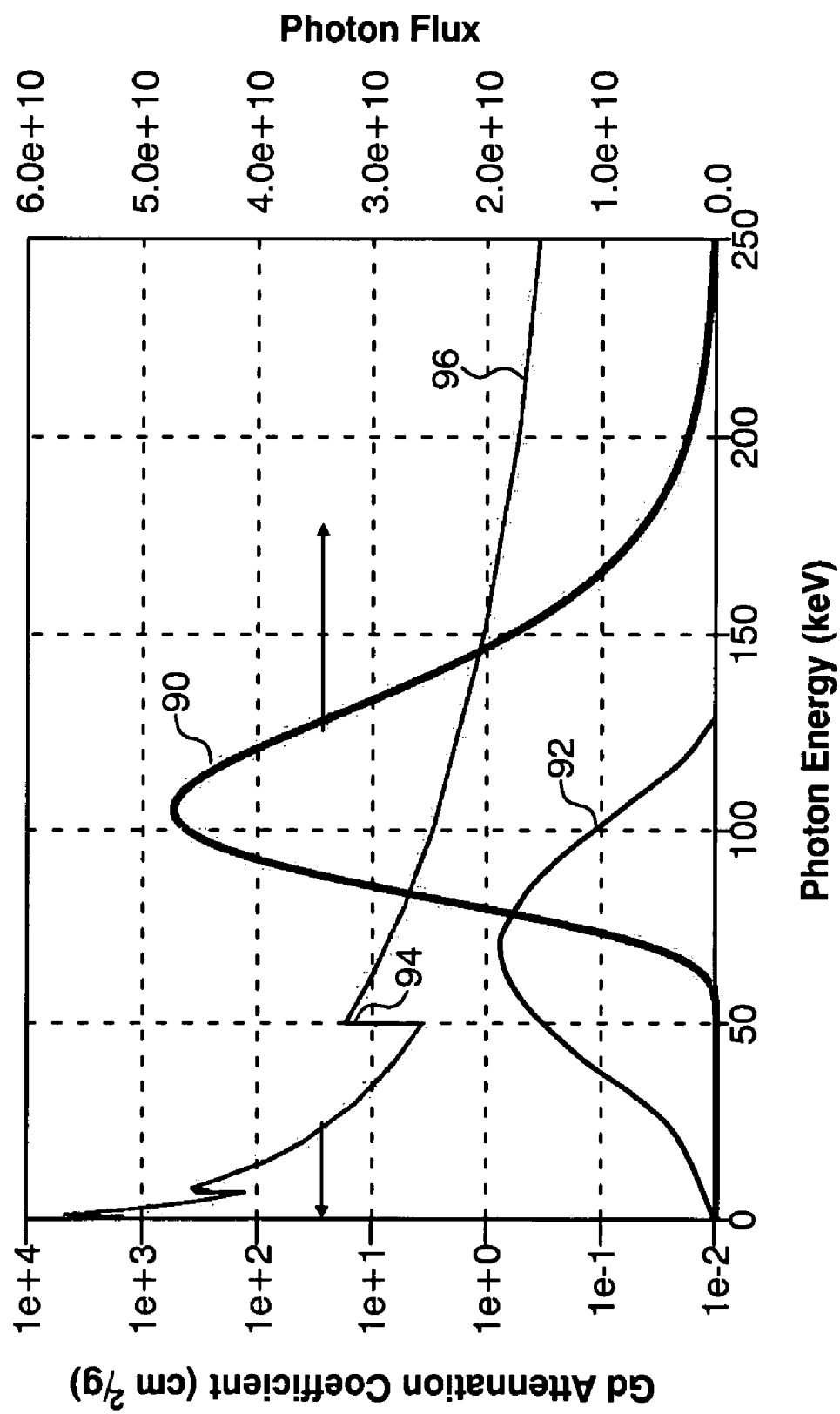
FIG. 8 is a plot of incident and scattered radiation spectra for a radiation scattering agent, gadolinium (Gd), of the present invention, superimposed over a plot of the attenuation coefficient of Gd.

Referring to FIG. 8, the scattering agent is preferably chosen so that it preferentially raises the valley dose compared to the peak dose. An incident energy spectrum 90 is quite far above the scatter's K-edge, close to the lower tail of the attenuation curve 96, so that it is not extensively absorbed in the material. A scattered energy spectrum 92 of X-rays scattered between the microbeams (i.e., in the valleys) is almost entirely above, or just above, the K-edge energy 94, so that the absorption of valley X-rays is enhanced. Preferably, the median energy of the incident energy spectrum 90 is substantially above the K-edge 94 of the substance. In FIG. 8, the scattering agent includes gadolinium, having a K-edge of 50.23 keV.

The target tissue of the method of the present invention includes a tumor, such as a brain tumor. The technique of enhancing the broad beam effect of the present invention for the treatment of brain tumors using radiation scattering agents capitalizes on two effects. First, because of the compromised blood-brain-barrier (BBB) in brain tumors (also known as blood-tumor barrier, BTB) compared to the normal brain, the tumor preferentially accumulates contrast agents. Second, as indicated by Monte Carlo simulations of the dose distribution in tissues from parallel arrays of microbeams, the presence of scattering agents in the tissue, such as the medium-size elements iodine and gadolinium, preferentially increases the tumor's valley dose (i.e., the radiation leakage between individual microbeams).

For example, Monte Carlo simulations of unidirectional MRT dose distributions in the rat brain for known uptake of gadolinium show a 3-fold increase in the valley dose and 1.5-fold increase in the peak dose of microbeams from an assumed 10 mg/cm3 uptake of gadolinium (Gd) in rat brain tumors 5 minutes after injection.

The physical effects underlying the preferential rise of the valley dose by contrast agents is the following. The valley dose is the radiation leakage between microbeams, caused in large part by Compton scattering of X-rays. The valley dose is an important dose in the microbeam dose distribution in terms of relationship to the tissue damage, because it is the dose that determines if cells (such as endothelial cells and progenitor glial cells) will survive between microbeams. Certain contrast agents act as scattering agents to preferentially increase the valley dose as follows. The average energy of the scattered X-rays that make up the valley dose is much lower than that of the incident energy spectrum of the unscattered X-rays in the microbeams (incident energy spectrum).

For example, an X-ray beam currently used for MRT research at a beamline of the National Synchrotron Light Source (NSLS), Brookhaven National Laboratory, Upton, N.Y., has a median beam energy of about 120 keV, which is far above the K-edge of common contrast agents. Iodine, for example, has a 33.17 keV K-edge, while gadolinium has a 50.23 keV K-edge. At the K-edge, the total attenuation coefficient of the X-rays jumps up by several folds depending on the element, but it gradually decreases back as the energy increases continuously beyond the K-edge, and it loses the K-edge gain by the time it departs several tens of keV from the K-edge.

The (scattered energy) spectrum of the scattered X-rays between unidirectional microbeams, however, which is mostly multiple Compton scattering, includes considerably lower energies than the incident beam, and approaches the K-edge of the contrast agent. Preferably, the scattered energy spectrum includes the K-edge energy. Therefore, the attenuation coefficient of the tissue for the X-rays that make up the valley dose is up to 2–3 fold larger than that of the X-rays that make the peak dose. Subsequently, the presence of the contrast agent preferentially inside the tumor will preferentially increase the valley dose in the tumor.

For gadolinium, for instance, the K-edge (i.e., the peak absorption energy) is about 50.23 keV, the mean energy of the peak dose is preferably about 120 keV, and that of the scattered radiation for a subject such as a rat head is then about 80 keV. Gadolinium's absorption coefficient at 80 keV is about 4 times larger than that at 120 keV. The mean energy of the beam for a subject of the size of the human head will be even lower than 80 keV, leading to an even larger preferential valley dose absorption in a human subject. The effect is, however, partially offset by the fact that a smaller amount of gadolinium will also reside in the normal brain tissue surrounding the brain tumor.

In a preferred embodiment of the method, the scattering agent includes a substance characterized by a K-edge energy, which preferentially raises the valley dose for an incident energy spectrum. The method preferably includes providing an incident energy spectrum that produces a scattered energy spectrum, which includes substantial radiation just above or entirely above the K-edge energy to enhance the absorption of valley X-rays.

EXAMPLE

The following study was carried out at the National Synchrotron Light Source (NSLS), Brookhaven National Laboratory, Upton, N.Y., 11973. The results show the efficacy of gold nanoparticles combined with BIMRT. Mice with subcutaneous murine mammary carcinoma tumor EMT-6 tumor inoculated behind their neck were treated with the BIMRT of the present invention. The microbeam arrays had a 0.68 millimeters (mm) beam thickness and 1.36 mm center-to-center beam spacing, i.e., 0.68 mm inter-beam spacing. The gold nanoparticles used in the study were about 1.9 nm in diameter. At the ninth day of inoculation, when the tumor sizes averaged about 100 mm3, the mice were randomized in five groups of seven (7) mice each for the following treatments: Group A: 55 Gy BIMRT; Group B: 55 Gy broad beams (bidirectional, 2×27.5 Gy); Group C: 35 Gy BIMRT; Group D: 35 Gy BIMRT with gold nanoparticles; and Group E: Unirradiated controls. The gold nanoparticles, 0.2 ml in volume, were injected via the tail vein 10–14 hours before the irradiations. In Group A, four (4) mice died from anesthesia problems.

The mice were positioned vertically in front of the beam inside a plastic tube. They were held by two horizontally positioned, near parallel, thin wooden rods that supported their jaws at the level of their neck, and were anchored in pairs of holes in the front and the back of the tube. The front of the nose was supported by cotton padding to keep the entire head vertical. They were irradiated anteroposteriorly (AP) and lateral. In both irradiations the irradiation field was 14 mm wide horizontally and 18–25 mm long depending on the size and the position of the tumor. The AP irradiations, which were centered symmetrically on the mouse's body axis, covered the entire width and height of the neck, including the salivary glands, trachea, esophagus, brain stem, and spinal cord. The lateral irradiations, however, were aimed at the tumor region only, with its edge positioned between the tumor and the rest of the mouse's body.

All positioning parameters were adjusted for each mouse, using frequent beam-positioning evaluation with a chromographic film. The line between the tumor and the rest of the body was delineated by using two thin wooden rods, as above, to squeeze the base of the tumor at the level of the back of the neck. This allowed guidance of the edge of the irradiation field. The goal was to have a 2 mm margin beyond the edge of the tumor. In this geometry, the entire normal tissue was only irradiated by the AP irradiation field. The tumor was confined in the target volume, which, for BIMRT, was subjected to both fields in the interlaced region. For the broad-beam irradiations, the target volume was irradiated by crossing (intersecting) both irradiation fields within the target volume which doubled the dose compared to that in the normal-tissue region.

Three months after irradiation, one mouse exposed to 55-Gy BIMRT (Group A) was still alive. In the 35-Gy group with gold injection (Group D), the tumors of two mice were ablated. Mice in all other groups died either from excessive tumor growth (including the 35-Gy no-gold group (Group C) and the unirradiated controls (Group E)) or from normal-tissue toxicity (including the 55-Gy broad-beam group (Group B)). The salivary-gland output test showed a 70% salivary output in the groups of 55-Gy BIMRT with no gold, and 35-Gy BIMRT with gold. Although the irradiation set up suffered from some imperfections, including, probably, small gaps between the interlaced beams in the tumor, these results are very promising. In particular, the results indicate that a) the mouse thyroid essentially tolerates 55-Gy microbeams of at least 680 μm thickness, and b) the therapeutic efficacy of gold-enhanced BIMRT at 35 Gy is better than or equal to that of 55 Gy BIMRT without gold, while the BIMRT geometry has also advantageously proven less toxic to normal tissue than conventional broad beam.

Although illustrative embodiments of the present invention have been described herein with reference to the accompanying drawings, it is to be understood that the invention is not limited to those precise embodiments, and that various other changes and modifications may be effected therein by one skilled in the art without departing from the scope or spirit of the invention.

The invention claimed is:

1. A method of performing radiation therapy on a subject comprising:
delivering a therapeutic dose of high energy electromagnetic radiation substantially only to a target tissue by generating a broad beam radiation effect substantially only within the target tissue, the broad beam radiation effect not being generated in non-target tissue, said delivering comprising irradiating the target tissue with at least two non-intersecting arrays of microbeams, said two non-intersecting arrays comprising a first array including at least a first and a second microbeam, said first and second microbeams defining two parallel, spatially distinct microbeam paths, and a second array comprising at least a third microbeam defining a third microbeam path, wherein said first and second microbeam arrays are interleaved substantially only within the target tissue, whereby said third microbeam path is angularly rotated and laterally translated with respect to said first and second microbeam paths, and whereby said third microbeam path crosses between, but does not intersect with, said first and second microbeam paths to form a substantially continuous broad beam of radiation substantially only within the target tissue.

2. The method of claim 1, wherein each of said first and second parallel, spatially distinct microbeams comprises a beam thickness, a beam width, and a beam plane, wherein the at least two non-intersecting arrays comprise parallel beam planes and an inter-beam spacing between adjacent microbeams, the inter-beam spacing in each of the at least two non-intersecting arrays being substantially equal to the beam thickness, said interleaving further comprising:
irradiating the target tissue in a first irradiation direction with said a first one of the at least two non-intersecting arrays of microbeams;
angularly displacing said a second one of the at least two non-intersecting arrays from the first one of the at least two non-intersecting arrays by rotating one of the subject and a source generating the at least two non-intersecting arrays about an axis positioned through a center of the target tissue, the axis being perpendicular to the parallel beam planes;
translating the second one of the at least two non-intersecting arrays in a direction parallel to said angular displacement axis by a distance substantially equal to the beam thickness; and
irradiating the target tissue in a second irradiation direction with the second one of the at least two non-intersecting arrays.

3. The method of claim 2, wherein the spacing is substantially equal to the beam thickness, and wherein the translating distance is substantially equal to the beam thickness.

4. The method of claim 2, wherein the at least two non-intersecting arrays of microbeams are angularly displaced by about ninety (90) degrees.

5. The method of claim 2, wherein the beam thickness is substantially in a range greater than or equal to about 20 micrometers and less than or equal to about 1000 micrometers.

6. The method of claim 2, wherein the beam thickness is substantially in a range greater than or equal to about 500 micrometers and less than or equal to about 1000 micrometers.

7. The method of claim 2, further comprising repeating the steps of angularly displacing, translating, and irradiating in the second irradiation direction a number of times, a total number of n irradiations covering a 360° angular space around the target tissue.

8. The method of claim 7, said angularly displacing further comprising angularly displacing by an amount substantially equal to 360 degrees divided by n, said translating comprising translating by a distance substantially equal to the beam thickness, wherein said spacing is substantially equal to the product of the beam thickness and (n−1).

9. The method of claim 2, wherein the target tissue comprises ocular melanoma, wherein the high energy electromagnetic radiation comprises X-ray radiation, and wherein each of the at least two parallel, spatially distinct microbeams comprises a dose fall off of less than about 30 micrometers, when used with a synchrotron source, and of less than about 1 millimeter when used with bremsstrahlung radiation.

10. The method of claim 1, wherein said delivering further comprises administering the therapeutic dose over more than one session in dose fractionations, a sum of the dose fractionations being substantially equal to the therapeutic dose.

11. The method of claim 10, wherein said delivering further comprises separating the more than one session over a time interval within a range of about 12 hours to about five days.

12. The method of claim 1, further comprising providing a concentration of a radiation contrast agent substantially only to the target tissue, the concentration enhancing an in-beam dose of the high energy electromagnetic radiation in each of the at least two parallel, spatially distinct microbeams of the at least two non-intersecting arrays interleaved substantially only within the target tissue.

13. The method of claim 12, wherein the radiation contrast agent comprises a K-edge of at least 65 keV.

14. The method of claim 12, wherein the radiation contrast agent comprises metal nanoparticles.

15. The method of claim 12, wherein the metal nanoparticles comprise at least one of tungsten and gold.

16. The method of claim 1, wherein the high energy electromagnetic radiation comprises X-ray radiation.

17. The method of claim 16, wherein the X-ray radiation comprises bremsstrahlung radiation.

18. The method of claim 1, wherein the target tissue comprises one of an ocular tumor and a brain tumor.

19. A method of performing radiation therapy on a subject comprising:
delivering a therapeutic dose of X-ray radiation substantially only to a target tissue by generating a substantially continuous broad beam of radiation substantially only to the target tissue, said delivering comprising:
irradiating the target tissue with at least two non-intersecting microbeam arrays, said two non-intersecting microbeam arrays comprising a first array including at least a first and a second microbeam, said first and second microbeams defining two parallel, spatially distinct microbeam paths, and a second array including at least a third and a fourth microbeam, said third and fourth microbeams defining two parallel, spacially distinct microbeam paths, wherein each of said microbeams comprises a beam thickness, a beam width, and a beam plane, and wherein the at least two non-intersecting arrays comprise parallel beam planes and an inter-beam spacing between adjacent microbeams, the inter-beam spacing in each of the at least two non-intersecting arrays being substantially equal to the beam thickness;
interleaving the at least two non-intersecting microbeam arrays substantially only within the target tissue, whereby said third and fourth microbeam paths are angularly rotated and laterally translated with respect to said first and second microbeam paths, and whereby said third microbeam path crosses between, but does not intersect with, said first and second microbeam paths to form the substantially continuous broad beam of radiation, said interleaving further comprising:
irradiating the target tissue in a first irradiation direction with said first one of the at least two non-intersecting arrays of microbeams;
angularly displacing said a second one of the at least two non-intersecting arrays from the first one of the at least two non-intersecting arrays by rotating one of the subject and a source generating the at least two non-intersecting arrays about an axis positioned through a center of the target tissue, the axis being perpendicular to the parallel beam planes;
translating the second one of the at least two non-intersecting arrays in a direction parallel to said angular displacement axis by a distance substantially equal to the beam thickness; and
irradiating the target tissue in a second irradiation direction with the second one of the at least two non-intersecting arrays.

20. The method of claim 19, further comprising providing a concentration of a radiation contrast agent substantially only to the target tissue, the concentration enhancing an in-beam dose of the X-ray radiation in each of the at least two parallel, spatially distinct microbeams of the at least two non-intersecting arrays interleaved substantially only within the target tissue.

21. The method of claim 20, wherein the radiation contrast agent comprises metal nanoparticles, the metal nanoparticles comprising at least one of tungsten and gold.

* * * * *